United States Patent
Dékany et al.

(10) Patent No.: US 9,012,625 B2
(45) Date of Patent: Apr. 21, 2015

(54) METHOD FOR THE SYNTHESIS OF A TRISACCHARIDE

(75) Inventors: Gyula Dékany, Queensland (AU);
Károly Ágoston, Telki (HU); Istvan Bajza, Debrecent (HU); Julien Boutet, La Plaine sur Mer (FR); Marie Bøjstrup, Tåstrup (DE); Mette Fanefjord, Lyngby (DE); Ignacio Pérez Figueroa, Miami, FL (US); Markus Hederos, Svedala (SE); Ferenc Horvath, Pilisszentkereszt (HU); Piroska Kovács-Pénzes, Jászberény (HU); Lars Kröger, Hamburg (DE); Johan Olsson, Stockholm (SE); Christoph Röhrig, Mühlingen (DE); Andreas Schroven, Barssel (DE); Ioannis Vrasidas, Thessaloniki (GR)

(73) Assignee: Glycom A/S, Lyngby (DK)

( * ) Notice: Subject to any disclaimer, the term of this patent is extended or adjusted under 35 U.S.C. 154(b) by 182 days.

(21) Appl. No.: 13/263,708

(22) PCT Filed: Apr. 7, 2010

(86) PCT No.: PCT/EP2010/054607
§ 371 (c)(1),
(2), (4) Date: Dec. 30, 2011

(87) PCT Pub. No.: WO2010/115934
PCT Pub. Date: Oct. 14, 2010

(65) Prior Publication Data
US 2013/0131334 A1    May 23, 2013

(30) Foreign Application Priority Data

Apr. 7, 2009 (DK) .......................... PA 2009 00469

(51) Int. Cl.
| | |
|---|---|
| C07H 3/00 | (2006.01) |
| C08B 37/00 | (2006.01) |
| C12P 19/04 | (2006.01) |
| C07H 1/06 | (2006.01) |
| C07H 1/08 | (2006.01) |
| C07H 3/06 | (2006.01) |
| C07H 15/04 | (2006.01) |
| C07H 15/203 | (2006.01) |
| C07H 1/00 | (2006.01) |

(52) U.S. Cl.
CPC .................. C07H 3/06 (2013.01); C07H 15/04 (2013.01); C07H 15/203 (2013.01); C07H 1/00 (2013.01)

(58) Field of Classification Search
None
See application file for complete search history.

(56) References Cited

U.S. PATENT DOCUMENTS

| | | |
|---|---|---|
| 5,438,124 A | 8/1995 | Matta et al. |
| 2011/0245488 A1 | 10/2011 | Salsini et al. |

FOREIGN PATENT DOCUMENTS

WO    WO2010/070616    6/2010

OTHER PUBLICATIONS

Pohl et al. Tetrahedron Letters, vol. 38, No. 40, pp. 6985-6988.*
Abbas S A et al., "Synthesis of 0-alpha-l-fucopyranosyl-(1->)-0-beta-d-galactophranosyl (1->4)-d-glucopyranose (2'-0-alpha-l-fucopyranosyl-lactose)", Carbohydrate Research, Jan. 15, 1981 (1981-0-15), vol. 88, No. 1, pp. 51-60, XP026743786, ISSN: 0008-6215, United Kingdom.
Fernandez-Mayoralas A et al., "Synthesis of 3- and 2'-fucosyl-lactose and 3,2'-difucosyl-lactose derivatives", Carbohydrate Research, Oct. 15, 1986, vol. 154, No. 1, pp. 93-101, XP026618813, ISSN: 008-6215(00)90025-9, United Kingdom.
Komba, S et al., "Synthesis and Biological Activities of Three Sulfated Sialyl Le Ganglioside Analogues for Clarifying the Real Carbohydrate Ligand Structure of L-Selectin", Biorganic & Medicinal Chemistry, May 16, 1996, vol. 4, No. 11, pp. 1833-1847, PII: S0968-0896(96)00165-4, United Kingdom.
Jain R K et al, "A convenient synthesis of O-$_x$-L-fucopyranosyl-(1→2)-O-β-D-glucopyranose (2'-O-$_x$-L-fucopyranosyllactose)", Carbohydrate Research, Jan. 3, 1991, vol. 212, pp. c1-c3.
Rencurosi, A et al, "Improvement on Lipase Catalysed Regioselective O-Acylation of Lactose: A Convenient Route to 2'-O-Fucosyl-lactose", J. Carbohydrate Chemistry, Sep. 5, 2001, vol. 20, No. 7-8, pp. 761-765, Novara, Italy.
Izumi M et al, "Synthesis of 5-Thio-L-fucose-Containing Disaccharides, as Sequence-Specific Inhibitors, and 2'-Fucosyllactose, as a Substrate of α-L-Fucosidases", J. Org. Chem., 1997, vol. 62, No. 4, pp. 992-998, Japan.

* cited by examiner

*Primary Examiner* — Layla Bland
(74) *Attorney, Agent, or Firm* — McHale & Slavin, P.A.

(57) ABSTRACT

The present invention relates to an improved synthesis of a trisaccharide of the formula (1), novel intermediates used in the synthesis and the preparation of the intermediates.

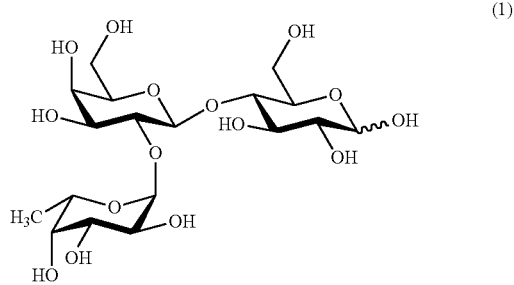

(1)

17 Claims, 3 Drawing Sheets

METHOD FOR THE SYNTHESIS OF A TRISACCHARIDE

CROSS-REFERENCE TO RELATED APPLICATIONS

This application is a §371 national stage entry of International Application No. PCT/EP2010/054607, filed Apr. 7, 2010, which claims priority to Denmark Patent Application No. PA 2009 00469, filed Apr. 7, 2009, the entire contents of which are incorporated herein by reference.

FIELD OF THE INVENTION

The present invention relates to an improved synthesis of a trisaccharide, novel intermediates used in the synthesis and the preparation of the intermediates.

BACKGROUND OF THE INVENTION

In the present years commercialization efforts for the synthesis of complex carbohydrates including secreted oligosaccharides have increased significantly due to their roles in numerous biological processes occurring in living organisms. Secreted oligosaccharides such as human milk oligosaccharides are becoming important commercial targets for nutrition and therapeutic industries. However, the syntheses and purification of these oligosaccharides and their intermediates remained a challenging task for science. One of the most important human milk oligosaccharides is 2'-O-fucosyllactose (α-L-fucopyranosyl-(1→2)-β-D-galactopyranosyl-(1→4)-D-glucose, "2'-FL") found in the highest concentration in mother's milk.

Scheme 1. The structure of 2'-O-fucosyllactose

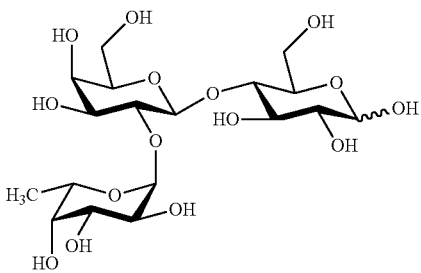

Several biological roles of 2'-O-fucosyllactose have been suggested including but not limited to its prebiotic, antibacterial, antiviral, immune system enhancing, brain development enhancing, etc. effects making it an attractive target for large scale production/isolation/purification for nutritional and therapeutic industries. 2'-O-fucosyllactose has been synthesised by both chemical and enzymatic methodologies but commercially attractive production processes have not been developed due to lack of efficient purification and synthetic approaches. According to present scientific knowledge 2'-O-fucosyllactose is not a crystalline trisaccharide making the development of large scale/low cost manufacturing technologies suitable for the manufacture of high purity 2'-O-fucosyllactose a challenging task.

It is possible to obtain 2'-O-fucosyllactose by four different approaches using isolation, chemical synthesis, enzymatic synthesis and biotechnological methodologies.

The first mentioning of HMO's in the literature appeared in the 1950's. At these times specific human milk oligosaccharides were isolated from human milk by using sophisticated chromatographic protocols. However, the purities of such early isolated samples are rather uncertain due to the high number of human milk oligosaccharide isomers present in mother's milk. For example, 2'-O-fucosyllactose and 3-O-fucosyllactose are both present in human milk and their chromatographic separation have been solved decades later. It has later been found that milk form other mammals also contain some of these oligosaccharides but in extremely low concentrations and ratios different from human milk. In the later years enormous progresses have been made in the production of 2'-O-fucosyllactose via chemical, enzymatic and biotechnological methodologies. However, most of these methodologies have not succeeded in large scale productions providing bulk quantities of 2'-O-fucosyllactose in a commercially attractive price range.

Enzymatic synthesis of 2'-O-fucosyllactose has developed significantly in the last decade by using enzyme cloning/mutating technologies. One specific approach has transferred a fucosidase enzyme into a 1,2-α-L-fucosynthase facilitating the synthesis of glycosidic linkages and avoiding hydrolysis of these at the same time. Unfortunately, 1,2-α-L-fucosynthases are not commercially available in large quantities and therefore to date are not suitable for manufacturing technology developments. A second enzymatic approach has been using α-(1→2)fucosyltransferase, α-(1→2)-L-galactosyltransferase for the creation of interglycosidic linkages. These enzymes are rather sensitive and not really suitable for large scale preparations. Additionally, such enzymes require sugar nucleotide type donors which are hardly available and are extremely expensive. A third enzymatic approach is based upon the use of retaining α-L-fucosidases but the achieved selectivities and yields are usually rather modest.

Either genetically engineered microorganisms or mammals are used in biotechnological methodologies for the synthesis of 2'-O-fucosyllactose. Such technologies use complex enzymatic systems facilitating both the biosynthesis of precursors and the required glycosylations. To date, such approaches face severe regulatory approval hurdles due to the use of genetically engineered organisms and potential contaminations of non-natural oligosaccharides.

Chemical syntheses have until now still been the most economically efficient way to produce 2'-O-fucosyllactose. The hurdles of large scale chemical synthesis are i.e. low stereoselectivities, low overall yields, use of sophisticated and expensive purification methodologies such as column chromatography, and the use of toxic reagents not suitable for food/therapeutic product developments.

In prior art, all syntheses have been using a lactose acceptor and a fully protected L-fucose donor as essential building blocks. The differences among approaches are related to different protecting group strategies, glycosylation methodologies and final purification policies. According to our best knowledge, the first chemical synthesis of 2'-O-fucosyllactose was published in 1981 [1] and since then four further chemical [2-5] and one chemoenzymatic [6] syntheses have been published.

The first chemical synthesis of 2'-O-fucosyllactose was published by K. L. Matta and co-workers in 1981 [1] using a 6-O-benzoylated lactose acceptor and a tri-O-benzylated α-fucopyranosyl bromide donor followed by successive removal of the protecting groups (Scheme 2). The synthesis comprises several chromatographic purification steps in the intermediate stages in order to reach a final intermediate E which contains only benzyl protective groups. Compound E was chromatographed and the purified sample was crystallized from methanol-ether as a dihydrate. However, this dihydrate proved to be rather inconvenient for the last deprotection (catalytic hydrogenolysis) step due to its awkward solubility. Thus the reduction was performed using a dilute solution of compound E in glacial acetic acid. After removing the catalyst the filtrate was evaporated and co-evaporated with methanol, toluene and abs. ethanol several times to afford the crude 2'-FL as a white amorphous solid.

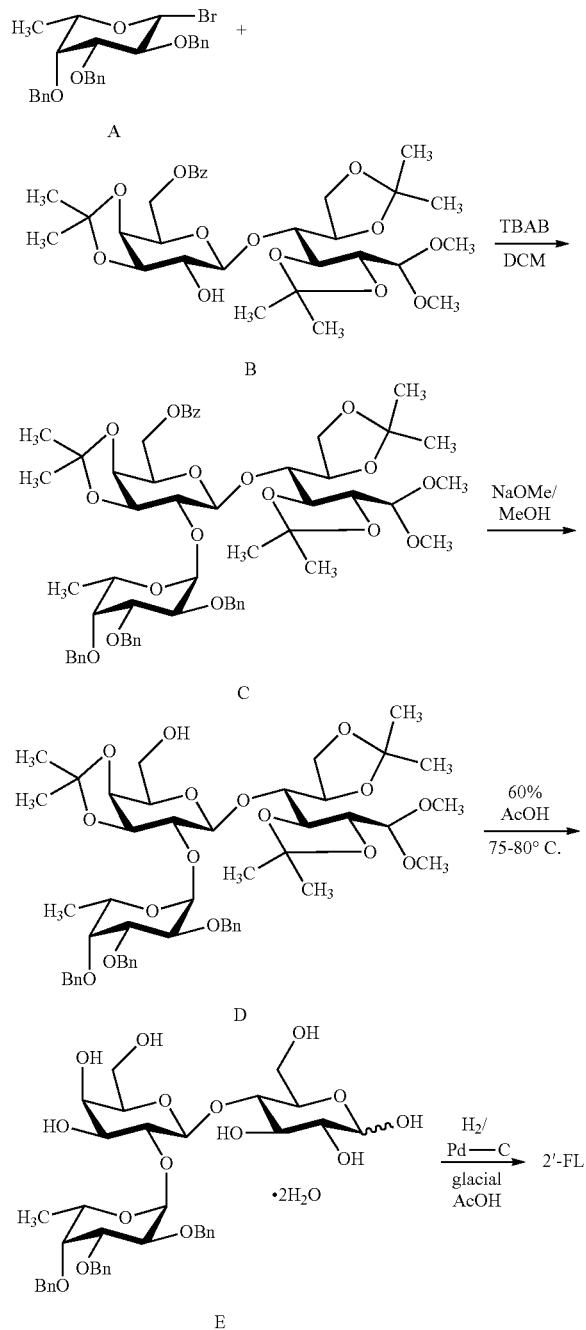

Scheme 2.

In 1986 M. Martin-Lomas [2] and co-workers published the synthesis of 2'-O-fucosyllactose preparing an isopropylidene-protected final 2'-FL intermediate. The final deprotection step is the cyclic ketal hydrolysis using 20% aqueous acetic acid. The synthetic strategy is utilizing a very rare lactose diol acceptor, which is difficult to make in large quantities. Actually, the precursor itself makes the approach uncompetitive for large scale technology developments. Furthermore, numerous chromatographic purifications are needed for intermediate isolations and the approach doesn't provide crystalline intermediates which might facilitate cheap purification options via crystallization. The final deprotection is a cyclic ketal hydrolysis which is a delicate step due to acid lability of the L-fucose residue. The hydrolytic cleavage condition of the cyclic ketal has to be rather gentle to prevent by-product formations. However, gentle hydrolysis conditions ends up with the presence of unhydrolyzed cyclic ketals in the reaction mixture. Thus, the crude 2'-O-fucosyllactose product requires further chromatographic purifications. Due to the disadvantages listed above the approach is not suitable for manufacturing technology developments.

K. L. Matta and co-workers published additional two syntheses [3, 4] choosing a protection group strategy which facilitated a trifluoroacetic acid assisted hydrolysis of the final 2'-FL intermediate. Both syntheses use the same acceptor but different 4-methoxybenzylated donor molecules. One approach uses n-pentenyl glycoside activated by IDCP while the second approach is based upon thioglycoside activation. The use of pentenyl glycoside with IDCP promoter prevents itself the development of production technologies due to the limited availability of the donor and the high price of the activator. In the case of thioglycoside activation, the fucosylation step provided an α/β-mixture in the ratio (9:1) and a rather difficult chromatographic purification was needed to separate the desired stereoisomer from the unwanted β-product. Thus, none of these methodologies have potentials for multi-ton-scale production of 2'-O-fucosyllactose.

In 1997 H. Hashimoto and co-workers developed a synthesis strategy using acid/oxidation labile protecting groups on both acceptor and donor molecules (isopropylidene and 4-methoxybenzyl) which were removed in trisaccharide intermediate via ceric ammonium nitrate treatment [5]. The approach provides polar products which are rather difficult to handle and contaminated by large quantity of ceric ammonium salts. Both the 2'-O-fucosyllactose and the inorganic impurity were water soluble substances, thus, O-acetylation followed by Zemplén deprotection was needed as the essential purification step of the synthesis. The approach has numerous drawbacks such as use of IDCP as a coupling reagent, removal of p-methoxybenzyl groups using CAN (expensive and toxic) and O-deacetylation of the final 2'-FL intermediate using sodium methoxide in the presence of base sensitive end-product. In general, high purity of 2'-O-fucosyllactose cannot be produced when reducing sugars are treated with strong bases.

In year 2001 L. Lay and co-workers introduced a synthesis of 2'-O-fucosyllactose using both enzymatic and chemical procedures [6]. In this approach a β-benzyllactoside derived acceptor was synthesized using enzymatic manipulations for installing orthogonal protecting groups in a regioselective manner. The last part of the synthetic strategy consists of three steps, the fucosylation, an O-deacetylation and a hydrogenolysis. Unfortunately, the method has never generated commercialization interest due to the relatively modest yields of lipase assisted acylation, the use of toxic and explosive hydrazine derivatives and lack of crystalline intermediates. Multiple chromatographic steps all along the synthesis prevented the development of manufacturing technologies.

In summary, isolation technologies have never been able to provide large quantities of human milk oligosaccharides including 2'-O-fucosyllactose due to the large number of oligosaccharides present in human milk. Additionally, the presence of regioisomers characterized by extremely similar structures further made separation technologies unsuccessful. Enzymatic methodologies suffer from the low availability of enzymes, extremely high sugar nucleotide donor prices and regulatory difficulties due to the use of enzymes produced in genetically modified organisms. The preparation of human milk oligosaccharides via biotechnology has huge regulatory obstacles due to the potential formation of several unnatural glycosylation products. To date, all the chemical methods developed for the synthesis of 2'-O-fucosyllactose have several drawbacks which prevented the preparation of even multigram quantities of 2'-O-fucosyllactose. The most severe drawback of chemical approaches is the lack of design for crystalline intermediates to facilitate low cost purification methodologies and to enhance scale-up opportunities. Thus, the demand for the development of a robust synthetic approach suitable for the production of 2'-O-fucosyllactose has been increasing.

The present invention provides methodologies suitable for both large scale manufacturing and large scale purification of 2'-O-fucosyllactose. The invention is based upon the utilisation of hydrogenolysis of O-benzyl/substituted O-benzyl moieties of novel protected 2'-O-fucosyllactose intermediates. Additionally, it is also an important characteristic of the present invention that the above-mentioned novel O-benzylated/substituted O-benzylated 2'-O-fucosyllactose intermediates have nice crystalline properties assisting powerful purification processes. For example, the realisation of highly crystalline properties of 2'-O-fucosyllactose derivatives allowed the development of powerful manufacturing procedures using entirely crystallisations for product/intermediate purifications. More importantly, the introduction of novel 2'-O-fucosyllactose intermediates provided by the present invention opens the very first opportunities for scale-up options. Before the present invention, complex reaction sequences had to be performed in a continuous manner due to lack of cheap purification options. The novel crystalline 2'-O-fucosyllactose intermediates allow the separation of chemical steps from each other providing real opportunities for scale-up developments. Thus, the crystalline novel intermediates provided by the present invention are responsible for the development of the very first 2'-O-fucosyllactose manufacturing technology suitable to give bulk quantities of high purity 2'-O-fucosyllactose for nutritional and pharmaceutical industries.

SUMMARY OF THE INVENTION

The first aspect of the present application relates to the use of compounds of general formula 1 for the preparation of 2'-O-fucosyllactose, characterized in that a compound of general formula 1

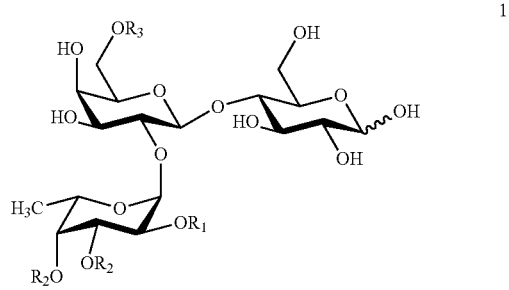

1 wherein $R_1$ and $R_2$, independently from each other, are a group removable by hydrogenolysis and $R_3$ is a group removable by hydrogenolysis or H— or a hydrate or solvate thereof is subjected to catalytic hydrogenolysis in a medium comprising water, or one or more $C_1$-$C_6$ alcohols or mixture thereof.

The second aspect of the present invention provides novel compounds of general formula 1

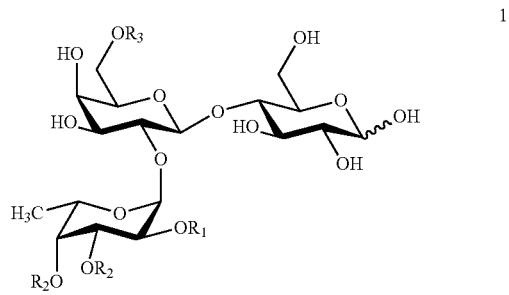

1 wherein $R_1$ and $R_2$, independently from each other, are a group removable by hydrogenolysis and $R_3$ is a group removable by hydrogenolysis or H— or a hydrate or solvate thereof, with the proviso that O-(2,3,4-tri-O-benzyl-α-L-fucopyranosyl)-(1→2)-O-β-D-galactopyranosyl-(1→4)-D-glucose dihydrate is excluded.

The third aspect of the present application is related to a method for the preparation of a group of novel compounds of general formula 1 according to the second aspect,

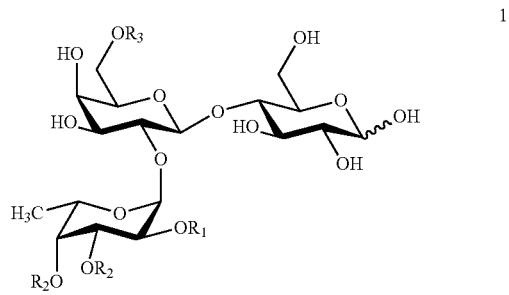

1 wherein $R_1$ and $R_2$, independently from each other, are a group removable by hydrogenolysis and $R_3$ is a group removable by hydrogenolysis or H, with the proviso when $R_3$ means H then at least one of the $R_1$ and $R_2$ groups is different from unsubstituted benzyl—or a hydrate or solvate thereof, characterized in that a compound of general formula 2

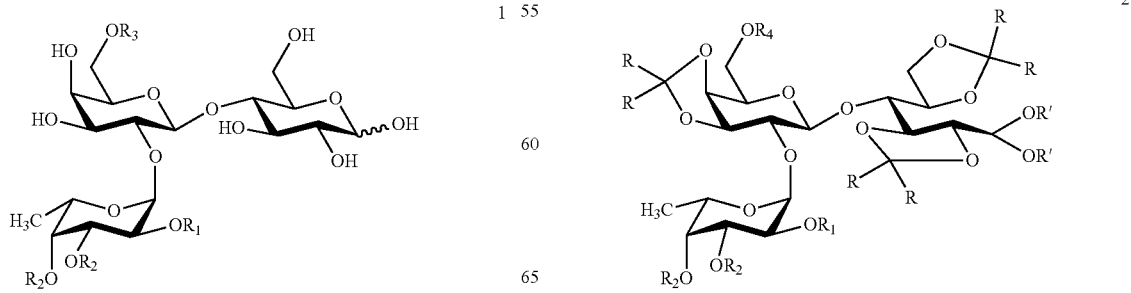

2 wherein R$_1$ and R$_2$, independently from each other, are a group removable by hydrogenolysis, R$_4$ is a group removable by hydrogenolysis, acetal type group, silyl or H, R is alkyl or two geminal R-groups with the carbon atom to which they are attached form a C$_3$-C$_6$ cycloalkyl ring, R' is alkyl, with the proviso when R$_4$ means acetal type group, silyl or H then at least one of the R$_1$ and R$_2$ groups is different from unsubstituted benzyl—or a hydrate or solvate thereof is subjected to acid catalyzed mild hydrolysis.

The fourth aspect of the present application relates to a method for the preparation of O-(2,3,4-tri-O-benzyl-α-L-fucopyranosyl)-(1→2)-O-β-D-galactopyranosyl-(1→4)-D-glucose free from crystalline water belonging to the compounds of general formula 1 according to the second aspect of the present application, comprising the steps of:
  a) acid catalyzed mild hydrolysis of a compound of general formula 2'

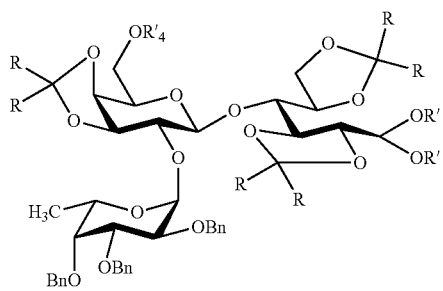

2' wherein R'$_4$ is acetal type group, silyl or H, R is alkyl or two geminal R-groups with the carbon atom to which they are attached form a C$_3$-C$_6$ cycloalkyl ring and R' is alkyl—or a hydrate or solvate thereof,
  b) collecting the product directly precipitated from the reaction mixture,
  c) recrystallization from a C$_1$-C$_6$ alcohol or a mixture of C$_1$-C$_6$ alcohols.

The fifth aspect of the present application relates to another method for the preparation of O-(2,3,4-tri-O-benzyl-α-L-fucopyranosyl)-(1→2)-O-β-D-galactopyranosyl-(1→4)-D-glucose free from crystalline water belonging to the compounds of general formula 1 according to the second aspect of the present application, comprising the steps of:
  a) acid catalyzed mild hydrolysis of a compound of general formula 2'

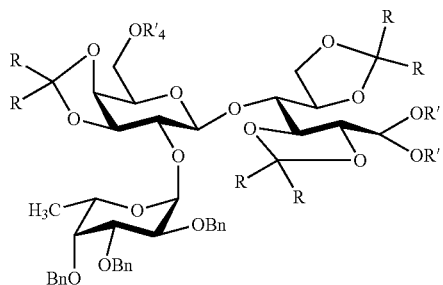

2' wherein R'$_4$ is acetal type group, silyl or H, R is alkyl or two geminal R-groups with the carbon atom to which they are attached form a C$_3$-C$_6$ cycloalkyl ring and R' is alkyl—or a hydrate or solvate thereof,
  b) dissolving the obtained material in a less polar aprotic solvent,
  c) extraction with water,
  d) isolation of the product,
  e) recrystallization from a C$_1$-C$_6$ alcohol or a mixture of C$_1$-C$_6$ alcohols.

The sixth aspect of the present application relates to another method for the preparation of O-(2,3,4-tri-O-benzyl-α-L-fucopyranosyl)-(1→2)-O-β-D-galactopyranosyl-(1→4)-D-glucose free from crystalline water belonging to the compounds of general formula 1 according to the second aspect of the present application, comprising the steps of:
  a) the crude product obtained according to the fourth aspect steps a-b) or according to the fifth aspect steps a-d) is dissolved in a more polar aprotic solvent,
  b) diluted with a less polar aprotic solvent,
  c) extracted with water and
  d) crystallized.

The seventh aspect of the present application relates to the method for the preparation of 2'-O-fucosyllactose, characterized in that a compound of general formula 1

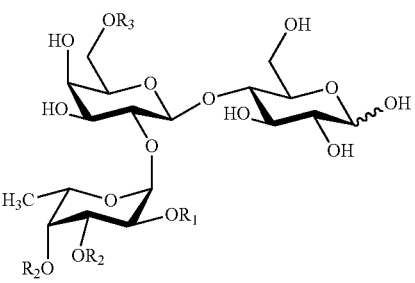

1 wherein R$_1$ and R$_2$, independently from each other, are a group removable by hydrogenolysis and R$_3$ is a group removable by hydrogenolysis or H— or a hydrate or solvate thereof is subjected to catalytic hydrogenolysis in a medium comprising water, or one or more C$_1$-C$_6$ alcohols, or mixtures thereof.

BRIEF DESCRIPTION OF THE FIGURES

The invention will be described in further detail hereinafter with reference to the accompanying figures, in which.

DETAILED DISCLOSURE OF THE INVENTION

Figure 1:
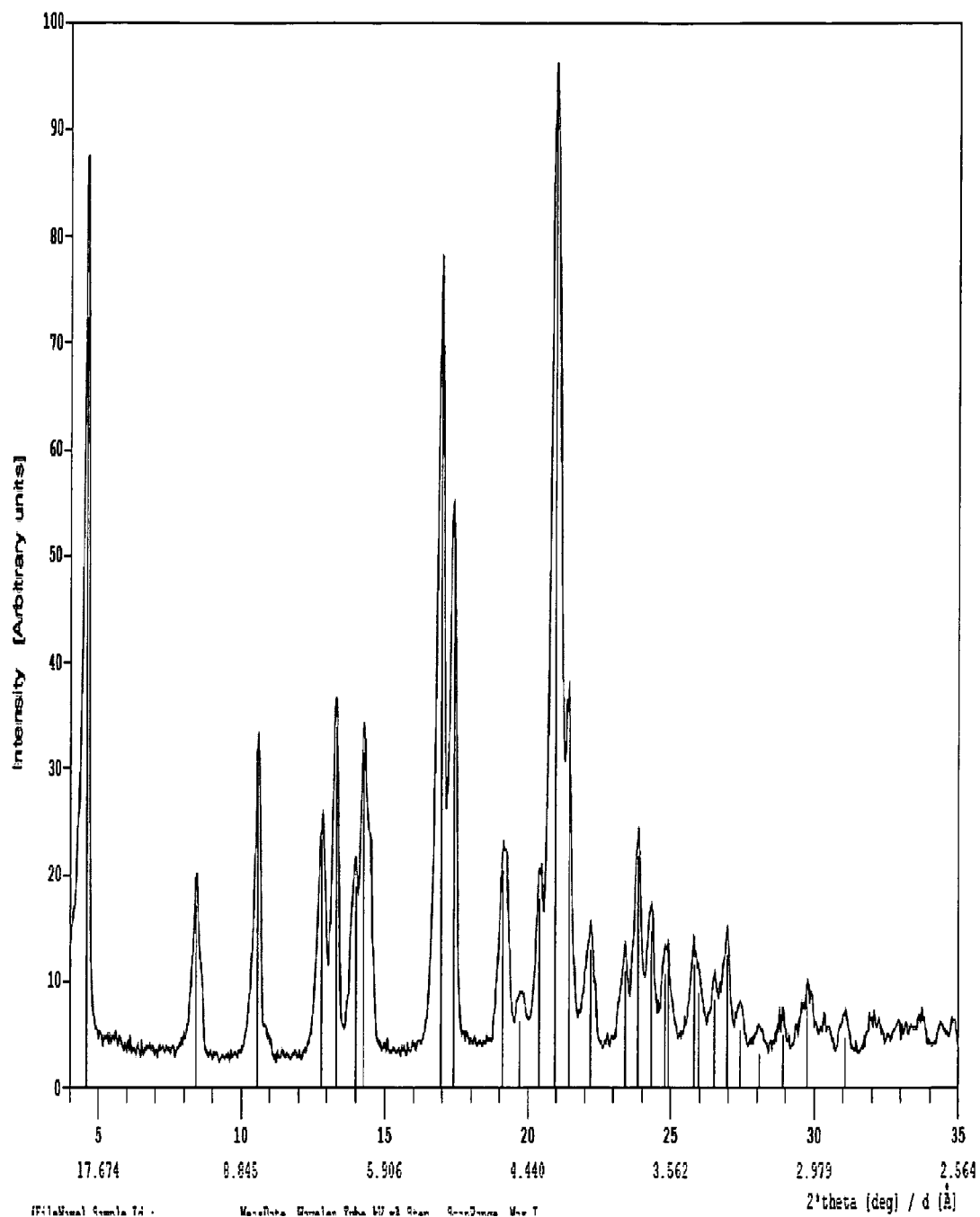
FIG. 1 shows an X-ray powder diffraction pattern of O-(2,3,4-tri-O-benzyl-α-L-fucopyranosyl)-(1→2)-O-β-D-galactopyranosyl-(1→4)-D-glucose free from crystalline water.

Throughout the present description, the term "alkyl" means a linear or branched chain saturated hydrocarbon group with 1-20 carbon atoms, preferably with 1-6 carbon atoms, like methyl, ethyl, n-propyl, i-propyl, n-butyl, i-butyl, s-butyl, t-butyl, n-hexyl, etc. The term "optionally substituted alkyl" intends to mean that the alkyl chain may either carry 1, 2, 3, 4 or 5 substituents or may be unsubstituted. The possible substituents, independently from each other, are selected from halogen, hydroxyl, optionally substituted alkyloxy, nitro, amino, optionally substituted alkylamino, optionally substituted dialkylamino, optionally substituted acyl, optionally substituted acylamino, carboxyl, optionally substituted alkyloxycarbonyl, carbamoyl, optionally substituted N-alkylcarbamoyl, optionally substituted N,N-dialkylcarbamoyl, optionally substituted N-arylcarbamoyl, thiol, optionally substituted alkylsulfanyl, optionally substituted aryl, optionally substituted aryloxy and optionally substituted aryloxycarbonyl. It is emphasized that the benzyl group is regarded as a member of substituted alkyls (i.e. phenylmethyl). Optionally substituted benzyl intends to mean optionally substituted phenyl (vide infra) attached to the methyl group, such as 4-methylbenzyl, 3-phenylbenzyl, 4-methoxybenzyl, etc.

In the present application, the term "aryl", either alone or when attached to another atom or group, refers to a homoaromatic group such as phenyl or naphthyl. If these groupings are "optionally substituted", they may either be unsubstituted or may bear 1, 2, 3, 4 or 5 groups including—independently from each other—optionally substituted alkyl, optionally substituted alkyloxy, halogen, nitro, amino, optionally substituted alkylamino, optionally substituted dialkylamino, optionally substituted acyl, optionally substituted acylamino, carboxyl, optionally substituted alkoxycarbonyl, carbamoyl, optionally substituted N-alkylcarbamoyl, optionally substituted N,N-dialkylcarbamoyl, thiol, optionally substituted alkylsulfanyl and optionally substituted phenyl.

In the present description, the term "acyl" represent an R"—C(=O)-group, wherein R" may be H, alkyl (see above) or aryl (see above), like formyl, acetyl, propionyl, butyryl, pivaloyl, benzoyl, etc. In case of "optionally substituted acyl", the alkyl or aryl residue may either be unsubstituted or may be substituted (vide supra) giving rise to acyl groups such as chloroacetyl, trichloroacetyl, 4-chlorobenzoyl, 4-nitrobenzoyl, 4-phenylbenzoyl, 4-benzamidobenzoyl, 4-(phenylcarbamoyl)-benzoyl, etc. If R means H or alkyl, the group is also named alkanoyl, and if R is aryl, the group is named aroyl.

The term "alkyloxy" or "alkoxy" means an alkyl group (see above) attached to the parent molecular moiety through an oxygen atom, such as methoxy, ethoxy, t-butoxy, etc. "Optionally substituted alkyloxy" or "optionally substituted alkoxy" refers to an alkyloxy group that may either be unsubstituted or may be substituted on the alkyl portion as defined above, such as trifluoromethoxy, 2,2,2-trichloroethoxy, etc.

"$C_3$-$C_6$ cycloalkyl" means cyclopropyl, cyclobutyl, cyclopentyl or cyclohexyl.

"$C_1$-$C_6$ alcohol" refers to hydroxy- or dihydroxy-alkanes having 1 to 6 carbon atoms such as methanol, ethanol, n-propanol, i-propanol, n-butanol, i-butanol, s-butanol, t-butanol, amylalcohol, n-hexanol, ethylene glycol, propylene glycol, etc.

"Halogen" means fluoro, chloro, bromo or iodo.

"Amino" refers to a —$NH_2$ group.

"Alkylamino" means an alkyl group (see above) attached to the parent molecular moiety through an —NH-group, such as methylamino, ethylamino, etc. "Optionally substituted alkylamino" refers to an alkylamino group that may either be unsubstituted or may be substituted on the alkyl portion as defined above.

"Dialkylamino" means two alkyl groups (see above), either identical or different ones, attached to the parent molecular moiety through a nitrogen atom, such as dimethylamino, diethylamino, etc. "Optionally substituted dialkylamino" refers to an dialkylamino group wherein at least one of the alkyl portions may either be unsubstituted or may be substituted as defined above.

"Acylamino" refers to an acyl group (see above) attached to the parent molecular moiety through an —NH-group, such as acetylamino (acetamido), benzoylamino (benzamido), etc. "Optionally substituted acylamino" is an acylamino group that may either be unsubstituted or may be substituted on the acyl portion as defined above.

"Carboxyl" denotes an —COOH group.

"Alkyloxycarbonyl" means an alkyloxy group (see above) attached to the parent molecular moiety through a —C(=O)-group, such as methoxycarbonyl, t-butoxycarbonyl, etc. "Optionally substituted alkyloxycarbonyl" is an alkyloxycarbonyl group that may either be unsubstituted or may be substituted on the alkyl portion as defined above, such as benzyloxycarbonyl, etc.

"Carbamoyl" is an $H_2N$—C(=O)-group.

"N-Alkylcarbamoyl" means an alkyl group (see above) attached to the parent molecular moiety through a —HN—C(=O)-group, such as N-methylcarbamoyl, etc. "Optionally substituted N-alkylcarbamoyl" is an N-alkylcarbamoyl group that may either be unsubstituted or may be substituted on the alkyl portion as defined above.

"N,N-Dialkylcarbamoyl" means two alkyl groups (see above), either identical or different ones, attached to the parent molecular moiety through a >N—C(=O)-group, such as N,N-methylcarbamoyl, etc. "Optionally substituted N,N-dialkylcarbamoyl" is a N,N-dialkylcarbamoyl group wherein at least one of the alkyl portions may either be unsubstituted or may be substituted as defined above.

"N-Arylcarbamoyl" is an aryl group (see above) attached to the parent molecular moiety through a —HN—C(=O)-group, such as N-phenylcarbamoyl, etc. "Optionally substituted N-arylcarbamoyl" is an N-arylcarbamoyl group that may either be unsubstituted or may be substituted on the aryl portion as defined above.

"Thiol" denotes a —SH group.

"Alkylsulfanyl" or "alkylthio" intends to mean an alkyl group (see above) attached to the parent molecular moiety through a sulphur atom, such as methylsulphanyl (methylthio), ethylsulphanyl (ethylthio), etc. "Optionally substituted alkylsulphanyl" refers to an alkylsulphanyl group that may either be unsubstituted or may be substituted on the alkyl portion as defined above.

"Aryloxy" means an aryl group (see above) attached to the parent molecular moiety through an oxygen atom, such as phenoxy, naphthyloxy, etc. "Optionally substituted aryloxy" refers to an aryloxy group that may either be unsubstituted or may be substituted on the aryl portion as defined above, such as 4-methoxy-phenoxy, 4-methylphenoxy, etc.

"Aryloxycarbonyl" means an aryloxy group (see above) attached to the parent molecular moiety through a —C(=O)-group, such as phenoxycarbonyl, etc. "Optionally substituted aryloxycarbonyl" is an aryloxycarbonyl group that may either be unsubstituted or may be substituted on the aryl portion as defined above.

"Azido" means a —$N_3$ group.

The synthesis of complex oligosaccharides such as 2'-O-fucosyllactose follows multistep synthetic pathways utilising protection and deprotection strategies. In spite of the diverse intermediate structures of oligosaccharide syntheses, the final synthetic targets are usually the unprotected oligosaccharides themselves featuring exclusive water solubility. Organic solvents commonly used in synthetic manufacturing processes are not suitable for the reactions of the very final stages of the oligosaccharide synthesis. Hydrogenolysis represents an exception among protecting group chemistries, in which water can be used as a solvent. Hydrogenolysis itself is a powerful deprotection process suitable to remove O-benzyl/substituted O-benzyl moieties from an oligosaccharide scaffold in almost a quantitative manner under extremely gentle conditions preventing by-product formations. It is also an advantage of hydrogenolysis as a final deblocking procedure within a complex synthetic pathway that only catalytic amount of reagents are required for the completion of the reaction providing exclusively toluene or substituted toluene derivatives as by-products. Both toluene and substituted toluene derivatives can easily be removed even in multi ton scales from water soluble oligosaccharide products via evaporation and/or extraction processes.

The preparation of a large number of per-O-benzylated oligosaccharides has been described in scientific literature before but these oligosaccharide derivatives are oils, syrups or amorphous solids rather than crystalline solids. However, the present invention provides examples when even simple O-benzylated novel oligosaccharides give crystalline solids due to careful structural designs such as controlling anomeric purities and/or creating apolar molecular regions by the introduction of multiple O-benzyl moieties into the most advanced oligosaccharide intermediates. On the other hand the present invention also utilises the high crystalline properties of oligosaccharide intermediates decorated with selected substituted O-benzyl protecting groups.

The combination of using hydrogenolysis of highly crystalline O-benzylated and/or substituted O-benzylated oligosaccharide intermediates creates the very base of potential oligosaccharide manufacturing technologies.

As stated above, many oligosaccharides give oils or syrups limiting manufacturing purification technologies to expensive chromatographies. The high water solubility and low organic solvent solubility of unprotected oligosaccharides further narrow the scopes of purification technologies to high cost reverse phase separations. The present invention provides an alternative low cost purification protocol for the preparation of unprotected oligosaccharides in high purities by converting crude oligosaccharide mixtures into crystalline O-benzylated/substituted O-benzylated oligosaccharides first, using crystallisation as a low cost purification tool in the second stage and removing the O-benzyl/substituted O-benzyl protecting groups in the final stage.

In fact, the present invention combines the highly advantageous features of hydrogenolysis, and the high crystalline properties of O-benzylated/substituted O-benzylated oligosaccharide intermediates.

The first aspect of the present invention relates to the use of compounds of general formula 1 for the preparation of 2'-O-fucosyllactose, characterized in that a compound of general formula 1

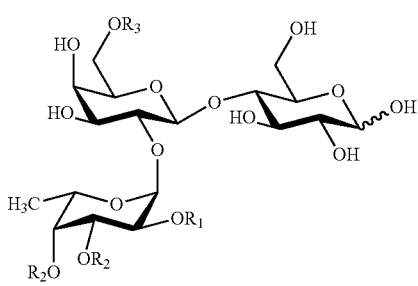

1 wherein $R_1$ and $R_2$, independently from each other, are a group removable by hydrogenolysis and $R_3$ is a group removable by hydrogenolysis or H—or a hydrate or solvate thereof is subjected to catalytic hydrogenolysis in a medium comprising water, or one or more $C_1$-$C_6$ alcohols or mixture thereof.

The term "a group removable by hydrogenolysis" refers to groups whose bond coupled to the oxygen splits easily by addition of hydrogen in the presence of palladium, Raney nickel or an appropriate metal catalyst resulting in the regeneration of the protected one or more OH-groups. This kind of protective groups is well-known to the person skilled in the art, many of them are referred to by P. G. M. Wuts and T. W. Greene: *Protective groups in organic synthesis* John Wiley & Sons (2007), including but not limited to benzyl, diphenylmethyl (benzhydryl), 1-naphthylmethyl, 2-naphthyl methyl, benzyloxymethyl, benzyloxycarbonyl or triphenylmethyl (trityl) groups, all of them may be optionally substituted by one or more alkyl, alkoxy, phenyl, amino, acylamino, alkylamino, dialkylamino, nitro, carboxyl, alkoxycarbonyl, carbamoyl, N-alkylcarbamoyl, N,N-dialkylcarbamoyl, azido, halogenalkyl or halogene on the aromatic ring(s).

The term "catalytic hydrogenolysis in a medium comprising water, one or more $C_1$-$C_6$ alcohols or mixtures thereof" intends to mean reduction with hydrogen in the presence of a catalyst that takes place in water, in a $C_1$-$C_6$ alcohol or mixture of $C_1$-$C_6$ alcohols, or in a mixture of water with one or more $C_1$-$C_6$ alcohols. The reaction milieu may contain organic acids (such as acetic acid, formic acid, propionic acid, chloroacetic acid, dichloroacetic acid, trifluoroacetic acid, etc.) and/or aprotic solvents miscible partially or fully with the organic acid(s), $C_1$-$C_6$ alcohol(s) or water (such as THF, dioxane, ethyl acetate, etc.). Water content of the reaction medium may be 0-100%, preferably 2-50%, more preferably 3-10%. Alcohol(s) may be present in the range of 0-100%, preferably 50-98%, more preferably 90-97%. Water, alcohol, water-alcohol mixtures or water-alcohol-acetic acid mixtures are preferably used as solvent system. Solutions containing the carbohydrate derivatives in 1-50 g/100 ml, preferably 3-33 g/100 ml, more preferably 6-12 g/100 ml concentrations are usually employed for the reaction, but suspensions are also applicable. The reaction mixture is stirred at 10-100° C. temperature range, preferably between 20-50° C. in hydrogen atmosphere of 1-50 bar in the presence of a catalyst such as palladium, Raney nickel or any other appropriate metal catalyst, preferably 2-10% palladium on charcoal or palladium black, until reaching the completion of the reaction. Catalyst metal concentrations generally range from 0.1% to 5.0% based on the weight of carbohydrate. Preferably, the catalyst concentrations range from 0.15% to 2.50%, more preferably 0.25% to 1.25%. Transfer hydrogenation may also be performed, when the hydrogen is generated in situ from cyclohexene, cyclohexadiene, formic acid or ammonium formate. The pH of the hydrogenolysis mixture is preferably neutral but organic or inorganic bases/acids and/or basic and/or acidic ion exchange resins can also be used to improve the kinetics of the hydrogenolysis. The use of basic substances is especially preferred when halogen substituents are present on the substituted benzyl moieties of the precursors. Acetic acid is favourably used as a co-solvent in cases when multiple benzyl groups have to be removed from the precursors in the range of 0.1-5.0 v/v %, preferably of 0.5-3.0 v/v %, more preferably of 0.75-1.25 v/v %. Preferred organic bases are including but not limited to triethylamine, diisopropyl ethylamine, ammonia, ammonium carbamate, diethylamine, etc. The conditions proposed allows to carry out the reduction in less volume using less solvent(s) and makes the possibility to study scale-up procedures and develop industrial method for producing 2'-FL. In addition, a simple, convenient and delicate removal of the solvent(s) can be applied giving rise to 2'-FL in excellent yield and high purity.

In one preferred embodiment 2'-O-fucosyllactose produced by methodologies of the present invention can be isolated as an amorphous solid by precipitation from water/organic solvent/aqueous solutions by cooling or by the addition of ethers including but not limited to MTBE, diethyl ether, diisopropyl ether etc. and/or $C_1$-$C_6$ alcohols. Alternatively 2'-O-fucosyllactose can also be isolated by freeze drying and spray drying.

In another preferred embodiment the hydrogenolysis of compounds characterized by general formula 1 is conducted using water or water-alcohol mixture as a solvent, 2-10% palladium on charcoal or palladium black as a catalyst in 1-10 atm of hydrogen pressure at 20-60° C. temperature. After the completion of the hydrogenolysis, the reaction mixture is filtered and preferably concentrated by removing the organic solvent components and subjected to precipitation, spray drying, freeze drying producing anhydrous and/or hydrated 2'-O-fucosyllactose (water content 0-20%) in a controlled manner.

In another preferred embodiment the hydrogenolysis of compounds characterized by general formula 1 is conducted using water or water-alcohol mixture as a solvent, 2-10% palladium on charcoal or palladium black as a catalyst in 1-10 atm hydrogen atmosphere pressure at 20-60° C. temperature. After the completion of the hydrogenolysis, the reaction mixture is filtered and preferably concentrated producing 2'-O-fucosyllactose aqueous solutions/syrup with a 2'-O-fucosyllactose concentration of 10-95%.

According to a preferred realization of the invention a compound of general formula 1, wherein $R_1$=$R_2$=benzyl and $R_3$ is H, in hydrated form or in a mixture of hydrated and crystalline water free forms is used in the hydrogenolysis.

In another preferred embodiment a compound of general formula 1, wherein $R_1$=$R_2$=benzyl and $R_3$ is H free from crystalline water is taken. Surprisingly, this anhydrous derivative shows excellent solubility in hot methanol (3 volumes) comparing to the dihydrate (which dissolves only partially in 10 volumes of hot methanol), allowing to carry out the reduction in less volume using less solvent(s). In addition, a simple, convenient and delicate removal of the solvent(s) can be applied affording 2'-FL in excellent yield and high purity.

Both solid forms of 2'-O-fucosyllactose such as amorphous/freeze dried/spray dried and liquid forms of 2'-O-fucosyllactose such as aqueous solutions/syrups provided by the present invention have high 2'-FL purity suitable for infant nutritional use including but not limited to infant formulas, infant cereals, clinical infant nutritional products etc. In general, both solid and liquid forms of 2'-O-fucosyllactose produced by the methodologies of the present invention are suitable for general nutritional use for infants, toddlers, children, adults and elderly. Both solid and liquid forms of 2'-O-fucosyllactose provided by the present invention can also be used as food additives, dietary supplements, a component of alcoholic and non alcoholic beverages such as soft drinks, fruit juices, bottled water, wine, beer etc. Both solid and liquid forms of 2'-O-fucosyllactose provided by the present invention can also be used as a therapeutic agent in broad therapeutic application areas including but not limited to prevent bacterial and viral infections, to avoid diarrhea, to enhance immune system and brain development, etc. Both solid and liquid forms of 2'-O-fucosyllactose provided by the present invention can also be used in veterinary applications including but not limited to fight against infectious diseases of domesticated animals. 2'-O-fucosyllactose provided by the present invention can also be used as a crucial monomer for the preparation of polymeric/polymer mounted products providing multivalent binding for bacteria and viruses. 2'-O-fucosyllactose provided by the present invention can also be used for the preparation of other human milk oligosaccharides by applying chemical and/or enzymatic methodologies including but not limited to simple structural modifications of further fucosylation, further sialylation, further extension of the core structure via N-acetyl lactosaminylation/N-acetyl-isolactosamination, etc.

The second aspect of the present invention provides novel trisaccharides characterized by general formula 1

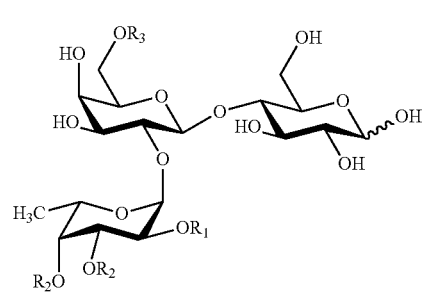

wherein $R_1$ and $R_2$, independently from each other, are a group removable by hydrogenolysis and $R_3$ is a group removable by hydrogenolysis or H—or a hydrate or solvate thereof, with the proviso that O-(2,3,4-tri-O-benzyl-α-L-fucopyranosyl)-(1→2)-O-β-D-galactopyranosyl-(1→4)-D-glucose dihydrate is excluded.

It is strongly emphasised that novel derivatives characterized by general formula 1 can be considered as sole chemical entities such as either α or β anomers or even an anomeric mixture of α and β isomers. Novel 2'-O-fucosyllactose intermediates of general formula 1 can be characterized as crystalline solids, oils, syrups, precipitated amorphous material or spray dried products. If crystalline, compounds of general formula 1 might exist either in anhydrous or in hydrated crystalline forms by incorporating one or several molecules of water into their crystal structures. Similarly, novel compounds characterized by general formula 1 might exist as crystalline substances incorporating ligands such as organic molecules and/or ions into their crystal structures.

In one preferred embodiment the novel trisaccharide is characterized by general formula 1 when $R_1$ and $R_2$ are, independently from each other, benzyl, 4-methylbenzyl, benzyloxycarbonyl, naphthylmethyl, 3-phenylbenzyl, 4-chlorobenzyl, 4-methoxybenzyl, 3,4-dimethoxybenzyl, 2,4,6-trimethylbenzyl or 2,3,4,5,6-pentamethylbenzyl, more preferably benzyl or 4-methylbenzyl and $R_3$ is H.

An even more preferred compound is O-(2,3,4-tri-O-benzyl-α-L-fucopyranosyl)-(1→2)-O-β-D-galactopyranosyl-(1→4)-D-glucose which is free from crystalline water

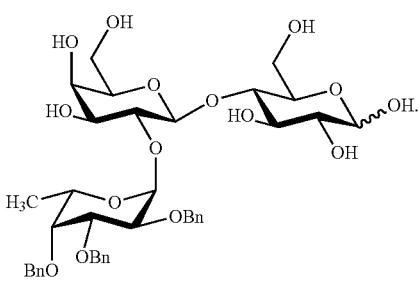

The crystalline water free O-(2,3,4-tri-O-benzyl-α-L-fucopyranosyl)-(1→2)-O-β-D-galactopyranosyl-(1→4)-D-glucose according to the present invention comprises X-ray diffraction reflection at 20.96±0.20 2θ, more preferably comprises X-ray diffraction reflections at 20.96±0.20 2θ and 16.95±0.20 2θ, even more preferably at 20.96±0.20 2θ, 16.95±0.20 2θ and 4.58±0.20 2θ, most preferably at 20.96±0.20 2θ, 16.95±0.20 2θ, 4.58±0.20 2θ and 17.40±0.20 2θ, in particular at one or more 2θ angles ±0.20 listed in the table below:

| 2Θ | rel. |
|---|---|
| 4.58 | 77 |
| 8.44 | 18 |
| 10.6 | 33 |
| 12.8 | 25 |
| 13.3 | 36 |
| 13.9 | 20 |
| 14.2 | 34 |
| 16.9 | 81 |
| 17.4 | 56 |
| 19.1 | 22 |
| 19.7 | 7 |
| 20.4 | 19 |
| 20.9 | 100 |
| 21.4 | 38 |
| 22.2 | 14 |
| 23.4 | 12 |
| 23.8 | 23 |
| 24.3 | 16 |
| 24.8 | 11 |
| 24.9 | 12 |
| 25.8 | 12 |
| 25.9 | 9 |
| 26.5 | 9 |
| 26.9 | 13 |
| 27.4 | 6 |
| 28.0 | 3 |
| 28.9 | 5 |
| 29.7 | 8 |
| 31.0 | 5 |

The XRPD pattern is shown in FIG. 1.

The crystalline water free O-(2,3,4-tri-O-benzyl-α-L-fucopyranosyl)-(1→2)-O-β-D-galactopyranosyl-(1→4)-D-glucose according to the present invention has a characteristic IR peak at 1078 cm$^{-1}$, preferably has characteristic IR peaks at 1078 and 1044 cm$^{-1}$, more preferably at 1078, 1044 and 3375 cm$^{-1}$, even more preferably at 1078, 1044, 3375 and 1384 cm$^{-1}$, in particular at one or more wavenumbers selected from 3375, 2929, 1462, 1454, 1402, 1384, 1078, 1044 cm$^{-1}$.

Figure 2:
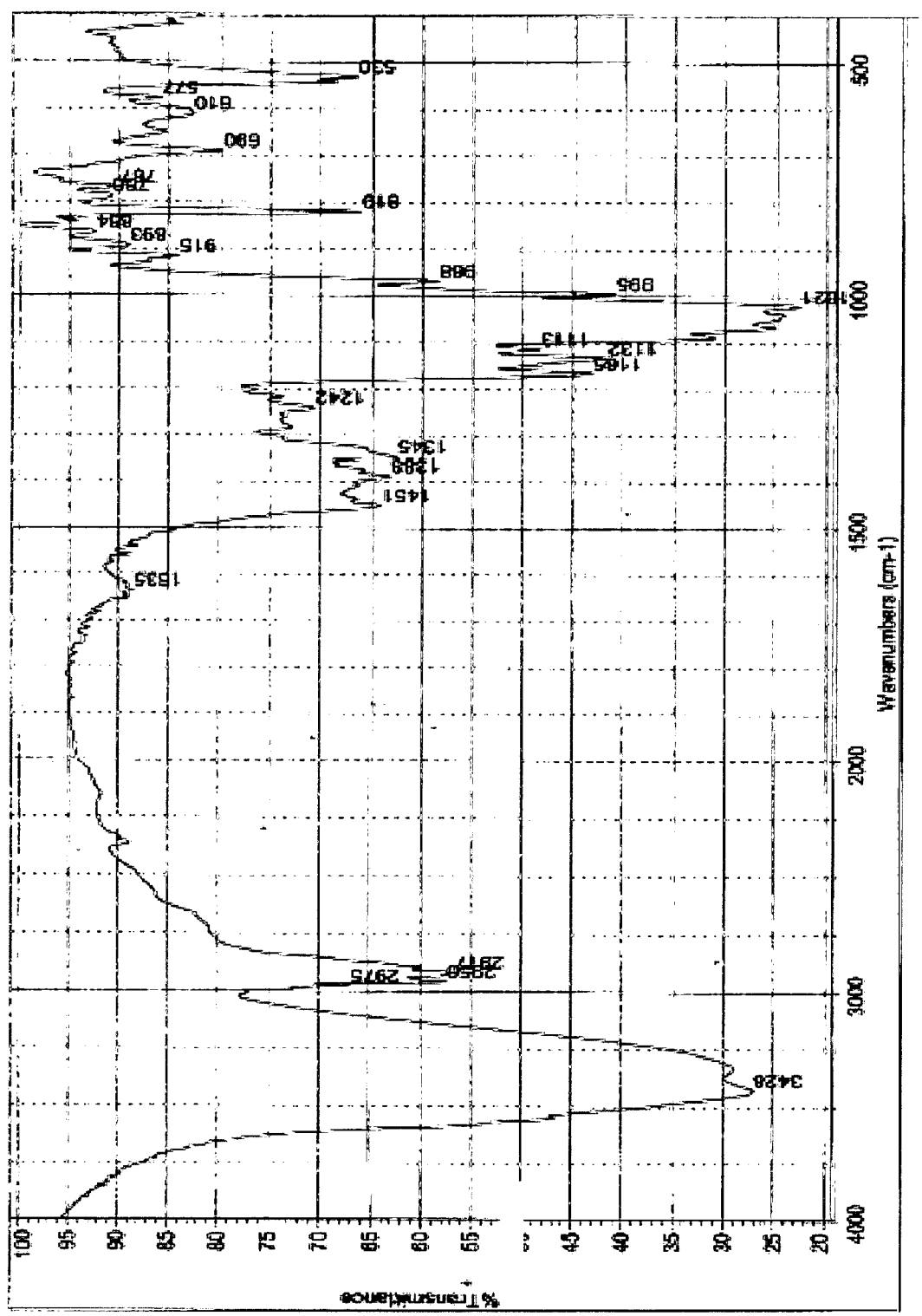
FIG. 2 shows the IR spectrum of O-(2,3,4-tri-O-benzyl-α-L-fucopyranosyl)-(1→2)-O-β-D-galactopyranosyl-(1→4)-D-glucose free from crystalline water.

The IR spectrum is shown in FIG. 2.

The crystalline water free O-(2,3,4-tri-O-benzyl-α-L-fucopyranosyl)-(1→2)-O-β-D-galactopyranosyl-(1→4)-D-glucose according to the present invention displays, in DSC investigations, an endotermic reaction with peak temperature at 212±5° C., more preferably at 212±4° C., even more preferably at 212±3° C., most preferably at 212±2° C., in particular at 212±1° C.

Figure 3:
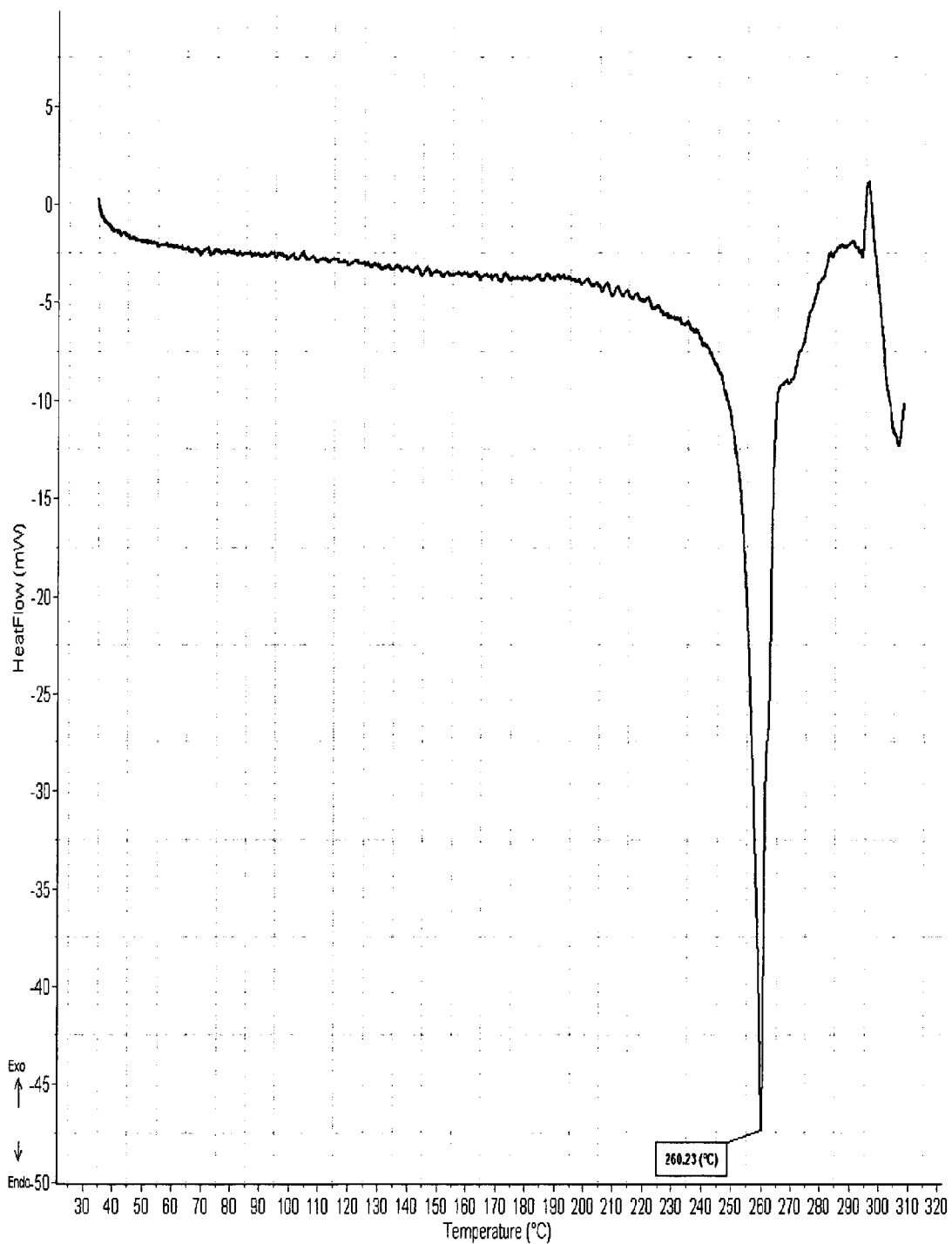
FIG. 3 shows a DSC recording of O-(2,3,4-tri-O-benzyl-α-L-fucopyranosyl)-(1→2)-O-β-D-galactopyranosyl-(1→4)-D-glucose free from crystalline water.

The DSC thermogram is shown in FIG. 3.

Novel compounds of general formula 1 provided by the present invention can be used for the preparation of 2'-O-fucosyllactose itself and other 2'-O-fucosyllactose derivatives by using chemical/enzymatic methodologies known in Art. Novel compounds of general formulas 1 can also be used as advanced precursors/intermediates for the production/preparation of numerous human milk oligosaccharides. Novel compounds of general formulas 1 can also be considered as valuable intermediates for the synthesis of complex oligosaccharides/glycoconjugates suitable for therapeutic/nutritional use.

The third aspect of the present invention provides a method for the preparation of a group of compound characterized by the general formula 1 according to the second aspect, wherein $R_1$ and $R_2$, independently from each other, are a group removable by hydrogenolysis and $R_3$ is a group removable by hydrogenolysis or H, with the proviso when $R_3$ means H then at least one of the $R_1$ and $R_2$ groups is different from unsubstituted benzyl—or a hydrate or solvate thereof, characterized in that a compound of general formula 2

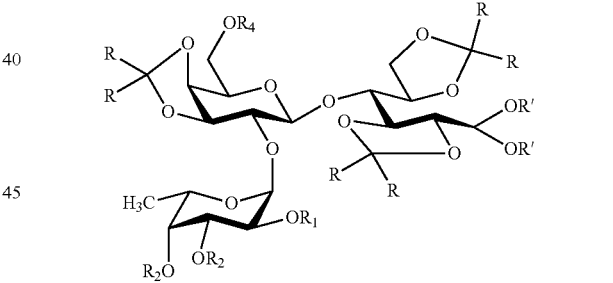

wherein $R_1$ and $R_2$, independently from each other, are a group removable by hydrogenolysis, $R_4$ is a group removable by hydrogenolysis, acetal type group, silyl or H, R is alkyl or two geminal R-groups with the carbon atom to which they are attached form a $C_3$-$C_6$ cycloalkyl ring, R' is alkyl, with the proviso when $R_4$ means acetal type group, silyl or H then at least one of the $R_1$ and $R_2$ groups is different from unsubstituted benzyl—or a hydrate or solvate thereof is subjected to acid catalyzed mild hydrolysis.

The term "acetal type group" means protective groups that with the oxygen atom of the hydroxyl group to be protected form a structure with two single bonded oxygens attached to the same carbon atom characterized by the following general structure:

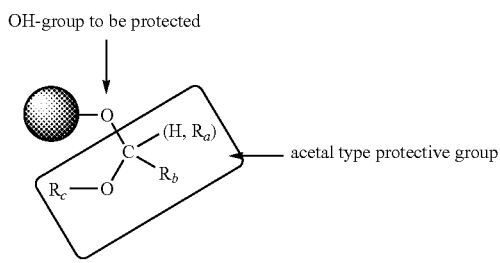

wherein $R_a$, $R_b$ and $R_c$ are carbon-bonded groups. This kind of groups is well-known to the person skilled in the art, many of them are referred to by P. G. M. Wuts and T. W. Greene: *Protective groups in organic synthesis* John Wiley & Sons (2007), including but not limited to methoxymethyl, t-butoxymethyl, 2-methoxy-ethoxymethyl, benzyloxymethyl, tetrahydropyranyl, tetrahydrofuranyl, 1,4-dioxan-2-yl, 1-methyl-1-methoxyethyl, 1-methyl-1-phenoxyethyl, etc. The acetal type protective groups are labile under mild acidic conditions.

The term "silyl group" means a protective group containing silicon atom covalently bonded to the oxygen atom of a hydroxy group to be protected (silyl ethers). This kind of groups is well-known to the person skilled in the art, many of them are referred to by P. G. M. Wuts and T. W. Greene: *Protective groups in organic synthesis* John Wiley & Sons (2007), including but not limited to trimethylsilyl, triisopropylsilyl, t-butyldimethylsilyl, t-butyldiphenylsilyl, etc. The silyl ethers are labile under mild acidic conditions.

The term "acid catalyzed mild hydrolysis" refers to a chemical reaction in which water reacts in the presence of acid at pH>2 with another substance bearing acid labile protective group(s) to regenerate the functional group(s) protected. In the present context the acid labile protective groups may be protective groups of primary or secondary hydroxyls (in the form of acyclic acetals or silyl ethers), 1,2-diol systems (in the form of cyclic acetals) or a formyl group (in the form of acetals). The starting compound may bear more than one acid labile protective groups that may be removed simultaneously or successively. In addition, the interglycosidic linkages may be also sensitive to acids. The skilled person is fully aware that interglycosidic linkages can be splitted by only strong acidic hydrolysis (pH<2). The skilled person is able to distinguish which deprotective condition affects the acetal and/or silyl groups while the interglycosidic linkages remain intact. Water—which has to be present in the reaction milieu as reagent—may serve as solvent or co-solvent as well. Organic protic or aprotic solvents which are stable under acidic conditions and miscible fully or partially with water such as $C_1$-$C_6$ alcohols, acetone, THF, dioxane, ethyl acetate, acetonitrile, etc. or mixture thereof may be used in a mixture with water. The acids used are generally protic acids selected from but not limited to acetic acid, trifluoroacetic acid, HCl, formic acid, sulphuric acid, perchloric acid, oxalic acid, p-toluenesulfonic acid, benzenesulfonic acid, cation exchange resins, etc., which may be present in from catalytic amount to large excess. The hydrolysis may be conducted at temperatures between 20° C. and reflux until reaching completion which takes from about 2 hours to 3 days depending on temperature, concentration and pH. Preferably, organic acids including but not limited to aqueous solutions of acetic acid, formic acid, chloroacetic acid, oxalic acid, etc. are used at 40-75° C.

Alternatively, anhydrous $C_1$-$C_6$ alcohols including but not limited to methanol, ethanol, propanol, butanol, etc. can also be used for the required cleavage of the acyclic/cyclic acetal/ketal moieties via acid catalyzed trans-acetalization/trans-ketalization processes. Catalytic amount of hydrogen chloride, sulphuric acid, perchloric acid, p-toluenesulfonic acid, acetic acid, oxalic acid, champhorsulfonic acid, strong acidic ion-exchange resins, etc. can be used for the purposes at temperatures of 20° C. to reflux. Preferably, methanol-acetonitrile 2:1 mixture is used in the presence of strong organic sulfonic acids such as p-toluenesulfonic acid or champhorsulfonic acid.

In a preferred embodiment the acid catalyzed mild hydrolysis is conducted in aqueous acetic acid solution at 40-75° C.

In another preferred embodiment a compound characterized by general formula 2, wherein R and R' mean methyl, one of the $R_1$ and $R_2$ groups or both $R_1$ and $R_2$ groups are 4-methylbenzyl and $R_4$ is H, is applied.

The fourth aspect of the present invention provides a method for the preparation of O-(2,3,4-tri-O-benzyl-α-L-fucopyranosyl)-(1→2)-O-β-D-galactopyranosyl-(1→4)-D-glucose free from crystalline water

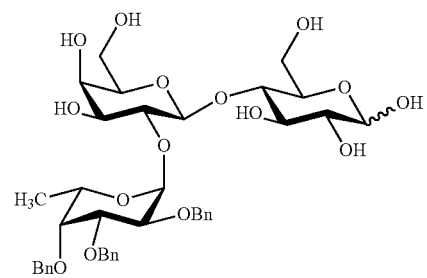

and belonging to novel compounds of general formula 1 according to the second aspect, comprising the steps of a) acid catalyzed mild hydrolysis of a compound of general formula 2'

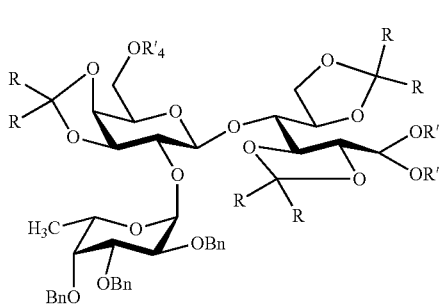

wherein $R'_4$ is acetal type group, silyl or H, R is alkyl or two geminal R-groups with the carbon atom to which they are attached form a $C_3$-$C_6$ cycloalkyl ring and R' is alkyl—or a hydrate or solvate thereof, b) collecting the product directly precipitated from the reaction mixture, c) recrystallization from a $C_1$-$C_6$ alcohol or a mixture of $C_1$-$C_6$ alcohols.

In a preferred embodiment a compound characterized by general formula 2', wherein R and R' mean methyl and $R'_4$ is H, is used for the hydrolysis.

After completion of the hydrolysis the deprotected trisaccharides may precipitate from the reaction mixture depending on the temperature, the solvent mixture used and concentration. Preferably precipitation takes place from a ternary solvent system containing ethyl acetate/acetonitrile/water wherein the proportion of the ethyl acetate is more than 40-45 v/v %, or from acidic aqueous THF solution wherein the acid is an aqueous solution of a strong inorganic acid such as HCl, sulphuric acid or perchloric acid in about 0.5-1 M concentration. The collected solids can then be recrystallized from a $C_1$-$C_6$ alcohol, preferably from methanol, ethanol and isopropanol, most preferably from methanol to yield O-(2,3,4-tri-O-benzyl-α-L-fucopyranosyl)-(1→2)-O-β-D-galactopyranosyl-(1→4)-D-glucose free from crystalline water. The volume of the $C_1$-$C_6$ alcohol used for recrystallization is about 2-8-fold in proportion to the air-dried mass of the trisaccharide to be recrystallized, preferably 2-5-fold, more preferably 2.5-3.5-fold. The recrystallization can be facilitated by adding seeding crystal.

The fifth aspect of the present application relates to another method for the preparation of O-(2,3,4-tri-O-benzyl-α-L-fucopyranosyl)-(1→2)-O-β-D-galactopyranosyl-(1→4)-D-glucose free from crystalline water belonging to the compounds of general formula 1 according to the second aspect of the present application, comprising the steps of:

a) acid catalyzed mild hydrolysis of a compound of general formula 2'

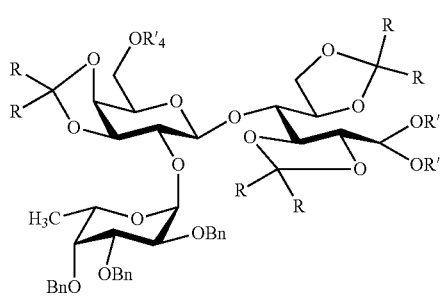

2' wherein $R'_4$ is acetal type group, silyl or H, R is alkyl or two geminal R-groups with the carbon atom to which they are attached form a $C_3$-$C_6$ cycloalkyl ring and R' is alkyl—or a hydrate or solvate thereof, b) dissolving the obtained material in a less polar aprotic solvent,
c) extraction with water,
d) isolation of the product,
e) recrystallization from a $C_1$-$C_6$ alcohol or a mixture of $C_1$-$C_6$ alcohols.

"Less polar aprotic solvent" intends to mean polar non-protogenic (not capable to act as proton donor) solvent whose dielectric constant is less than ca. 15 such as chloroform, n-butyl acetate, chlorobenzene, ethyl acetate, n-butyl chloride, dichloromethane, 1,4-dichlorobenzene, ethylene dichloride, methyl isobutyl ketone, tetrahydrofuran, pyridine, etc.

The target trisaccharide precipitated directly from the reaction mixture may contain polar mono- or disaccharides, mainly lactose, due to acid catalyzed decomposition. The progression of the decomposition can be followed by TLC and the ratio of the decomposed by-product(s) compared to the target trisaccharide can be estimated by TLC studies. If the precipitated solid fails to recrystallize from a $C_1$-$C_6$ alcohol due to a relatively high amount of polar by-product(s), the solid is redissolved in a less polar aprotic solvent such as ester type solvent like ethyl acetate, n-butyl acetate, etc. or such as chlorinated solvent like DCM, chloroform, ethylene dichloride, n-butyl chloride, chlorobenzene, etc., preferably ester type solvent, more preferably ethyl acetate, and washed with water in order to remove the polar contaminations. The product then precipitates or crystallizes out from the organic phase which can be recrystallized from a $C_1$-$C_6$ alcohol, preferably from methanol, ethanol and isopropanol, most preferably from methanol to give O-(2,3,4-tri-O-benzyl-α-L-fucopyranosyl)-(1→2)-O-β-D-galactopyranosyl-(1→4)-D-glucose free from crystalline water. The volume of the $C_1$-$C_6$ alcohol used for recrystallization is about 2-8-fold in proportion to the air-dried mass of the trisaccharide to be recrystallized, preferably 2-5-fold, more preferably 2.5-3.5-fold. The recrystallization can be facilitated by adding seeding crystal.

After completion of the hydrolysis the deprotected trisaccharides may be obtained as crude oil or syrup from the reaction mixture by evaporation of the solvent(s), which can be redissolved in a less polar aprotic solvent such as ester type solvent like ethyl acetate, n-butyl acetate, etc. or such as chlorinated solvent like DCM, chloroform, ethylene dichloride, n-butyl chloride, chlorobenzene, etc., preferably ester type solvent, more preferably ethyl acetate, and washed with water in order to remove the polar contaminations. The product then precipitates or crystallizes out from the organic phase which can be recrystallized from a $C_1$-$C_6$ alcohol, preferably from methanol, ethanol and isopropanol, most preferably from methanol to give rise to O-(2,3,4-tri-O-benzyl-α-L-fucopyranosyl)-(1→2)-O-β-D-galactopyranosyl-(1→4)-D-glucose free from crystalline water. The volume of the $C_1$-$C_6$ alcohol used for recrystallization is about 2-8-fold in proportion to the air-dried mass of the trisaccharide to be recrystallized, preferably 2-5-fold, more preferably 2.5-3.5-fold. The recrystallization can be facilitated by adding seeding crystal.

According to a more preferred embodiment a compound characterized by general formula 2' is treated with aqueous acetic acid solution at 60-75° C., preferably with 60 75% aqueous acetic acid solution, the solvents are evaporated to obtain an oily residue, which is redissolved in 4-6 volumes of ethyl acetate, extracted with water once or two times, and the crystals precipitated from the organic phase is recrystallized from methanol to obtain O-(2,3,4-tri-O-benzyl-α-L-fucopyranosyl)-(1→2)-O-β-D-galactopyranosyl-(1→4)-D-glucose free from crystalline water.

The sixth aspect of the present application relates to another method for the preparation of O-(2,3,4-tri-O-benzyl-α-L-fucopyranosyl)-(1→2)-O-β-D-galactopyranosyl-(1→4)-D-glucose free from crystalline water belonging to the compounds of general formula 1 according to the second aspect of the present application, comprising the steps of:

a) the crude product obtained according to the fourth aspect steps a-b) or according to the fifth aspect steps a-d) is dissolved in a more polar aprotic solvent,
b) diluted with a less polar aprotic solvent,
c) extracted with water and
d) crystallized.

"More polar aprotic solvent" intends to mean polar non-protogenic (not capable to act as proton donor) solvent whose dielectric constant is more than ca. 15 such as methyl ethyl ketone, acetone, N-methylpyrrolidone, dimethylformamide, dimethylacetamide, acetonitrile, DMSO, hexamethylphosphoramide, nitrobenzene, nitromethane, etc.

In a preferred embodiment a compound characterized by general formula 2', wherein R and R' mean methyl and $R'_4$ is H, is used for the hydrolysis.

Crude compounds obtained from a less polar aprotic solvent according to the fourth or fifth aspect of the present invention can be redissolved in a more polar aprotic solvent, preferably DMSO, DMF, dimethylacetamide or N-methylpyrrolidone, more preferably DMSO. The volume of the more polar aprotic solvent used is preferably 0.8-1.2-fold in proportion to the air-dried mass of the trisaccharide. The solution obtained is diluted with a less polar aprotic solvent such as ester type solvent like ethyl acetate, n-butyl acetate, etc. or such as chlorinated solvent like DCM, chloroform, ethylene dichloride, n-butyl chloride, chlorobenzene, etc., preferably ester type solvent, more preferably ethyl acetate. The volume of the less polar aprotic solvent used is preferably 2-7-fold, more preferably 3-5-fold in proportion to the more polar aprotic solvent used. The solution of the trisaccharide in the less and more polar aprotic solvents is then extracted with water several times, preferably 1-2 times. Crystals tend to precipitate upon standing which then are filtered, washed with cold less polar aprotic solvent used and dried to get O-(2,3,4-tri-O-benzyl-α-L-fucopyranosyl)-(1→2)-O-β-D-galactopyranosyl-(1→4)-D-glucose free from crystalline water.

According to a preferred embodiment a compound characterized by general formula 2' is treated with aqueous acetic acid solution at 60-75° C., preferably with 60-75% aqueous acetic acid solution, the solvents are evaporated to obtain an oily residue, which is redissolved in ethyl acetate, extracted with water once or two times, and the crystals precipitated from ethyl acetate are redissolved in DMSO, diluted with ethyl acetate, washed with water and the O-(2,3,4-tri-O-benzyl-α-L-fucopyranosyl)-(1→2)-O-β-D-galactopyranosyl-(1→4)-D-glucose free from crystalline water is crystallized out from the organic phase.

Compounds characterized by general formula 2 or 2' can be produced by standard methodology (Scheme 3). L-Fucose is peracetylated then L-fucose tetraacetate is thiolized with thiophenol in the presence of a Lewis acid to give phenyl 2,3,4-tri-O-acetyl-1-thio-β-L-fucopyranoside. Removal of the acetyl groups is achieved under Zemplén condition and the resulting triol is treated with dimethoxy-propane/acid to form the 3,4-acetonide. The free OH-group in the $2^{nd}$ position is then deprotonated with NaH and the alcoholate is reacted with $R_1$-halogenide, wherein $R_1$ is defined above, to give compounds of general formula 3. The isopropylidene-acetal is removed with acidic hydrolysis and the liberated OH-groups are protected by means of NaH/$R_2$-halogenide system, wherein $R_2$ is defined above, to yield compounds of general formula 4. When the same reaction is performed with phenyl 1-thio-β-L-fucopyranoside, compounds of general formula 4, wherein $R_1=R_2$ can be obtained. Compounds of general formula 4 are used as glycosyl donor in the glycosylation reaction.

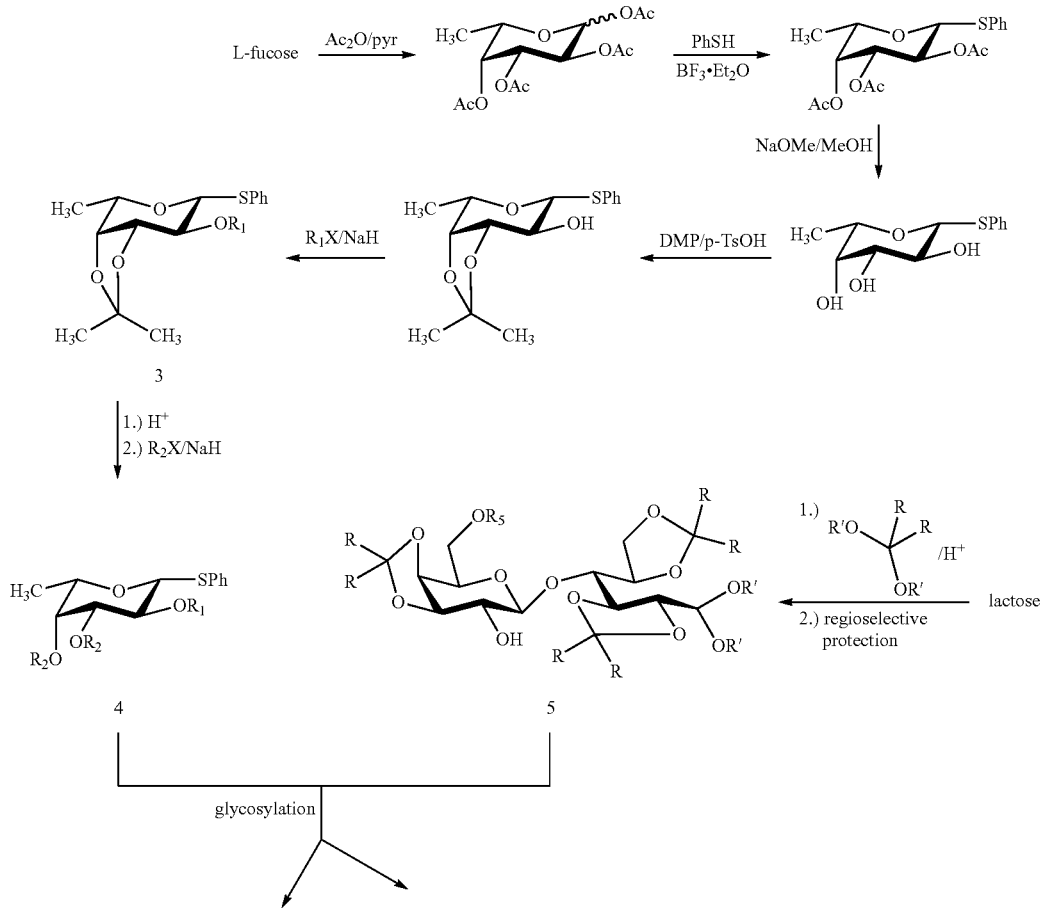

Scheme 3.

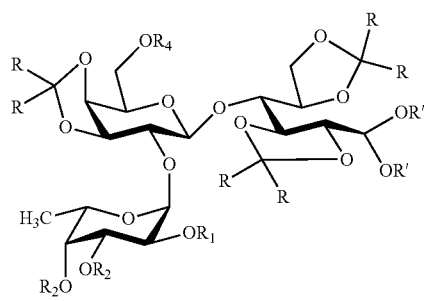
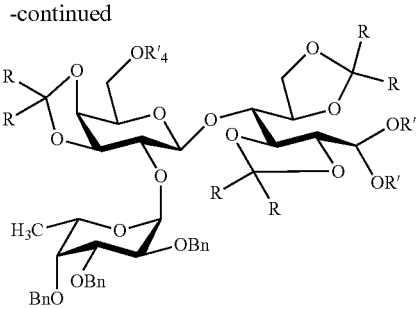

$R_4$ = acyl  
$R_4$ = OH  } NaOMe/MeOH $R'_4$ = acyl  
$R'_4$ = OH  } NaOMe/MeOH 2              2'

The glycosyl acceptor 5 can be synthesized from lactose in two steps. Treatment of lactose with dialkoxy ketal of a symmetric ketone at reflux in the presence of acid such as p-toluenesulfonic acid gives rise to 2,3:5,6-di-O-alkylidene-4-O-(3,4-O-alkylidene-β-D-galactopyranosyl)-D-glucose dialkyl acetal. The selective 6'-O-substitution of the primary hydroxyl group of lactose ketonide diol can be achieved for example with base catalysed reactions including $R_1$-halides to give compounds of general formula 5 wherein $R_6$ is a group removable by hydrogenolysis. Both inorganic and organic bases including but not limited to sodium hydride, potassium tert-butoxide, potassium hydroxide, sodium hydroxide, potassium carbonate, diisopropyl ethylamine, 1,8-diazabicyclo[5.4.0]undec-7-ene are suitable to catalyse such selective 6'-O-substitution processes of lactose ketonide diol. Such reactions can be performed either in homogeneous solutions using solvents such as DMF, THF, dioxane etc. or in aqueous phase transfer alkylation conditions. Preferably, NaH or potassium tert-butoxide is used in dioxane or DMF at 20-80° C. The selective 6-O-acylation can be conducted with traditional acylating agents like acyl halides, anhydrides, active esters, etc. in the presence of pyridine, triethylamine, diisopropyl ethylamine using in organic solvents such as DCM, chloroform, THF, dioxane, acetonitrile, etc. or mixture thereof at −20-80° C. to yield compounds of general formula 5 wherein $R_6$ is optionally substituted acyl. Selective acyclic acetal formation of lactose acetonide diol on the 6'-position can be performed with for example methoxymethyl, t-butoxymethyl, 2-methoxyethyl, benzyloxymethyl, 2-tetrahydrofuranyl, etc. halogenides, in the presence of triethylamine, morpholine, diisopropyl ethylamine, pyridine, etc., or with for example dihydropyran, 1,4-dihydrodioxin, dihydrofuran, 2-methoxypropene, 2-phenoxypropene, etc. in the presence of acids in organic solvents such as DMF, THF, dioxane, acetonitrile, etc. at 0-60° C. temperature to give rise to compounds of general formula 5 wherein $R_6$ is acetal type group. Selective primary OH-silylation reaction of the lactose acetonide diol with a silyl chloride in the presence of an amine base (such as imidazole, triethyl amine, etc.) at room temperature or with a silyl triflate with a hindered amine base (e.g. 2,6-lutidine) at low temperature can lead to compounds of general formula 5 wherein $R_6$ is silyl.

The coupling of donors 4 and acceptors 5 is conducted in aprotic solvent, preferably in dichloromethane, DMF, THF, toluene, acetonitrile or in mixtures thereof, more preferably in dichloromethane/DMF mixture, at temperatures between −78-0° C., in the presence of a thiofilic activator such as mercury(II) salts, $Br_2$, $I_2$, NBS, NIS, triflic acid, triflate salts, $BF_3 \cdot Et_2O$, TMSOTf, DMTST, phenylselenyl triflate, IDPC, tetrabutylammonium bromide or mixtures thereof, preferably $Br_2$/TBAB. The glycosylation reactions proceed with complete diastereoselectivity under exclusive formation of the (1α→2)-glycosidic linkage. In a typical experiment a mixture of bromine (1.2 eq.) in DCM is added dropwise to an ice-cooled solution of donor 4 (1.0 eq.) in DCM. A mixture of acceptor 5 (1.0 eq.) and TBAB (0.1 eq.) in DMF is dropped to the reaction mixture. The stirring is continued at room temperature until reaching completion. After extractive work-up the product is purified by either crystallization or by flash chromatography to give the compounds of general formulae 2 and 2', wherein $R_1$ and $R_2$, independently from each other, are a group removable by hydrogenolysis, $R_4$ and $R'_4$ are a group removable by hydrogenolysis, acetal type group, silyl or optionally substituted acyl, R is alkyl or two geminal R-groups with the carbon atom to which they are attached form a $C_3$-$C_6$ cycloalkyl ring and R' is alkyl. Before mild acidic hydrolysis the acyl derivatives (wherein $R_4$ and $R'_4$ are optionally substituted acyl) are converted to the corresponding primary alcohols (wherein $R_4$ and $R'_4$ are H). A manner to deacylate may be base catalyzed transesterification deprotection that is the acyl protective groups from hydroxyls are removed in an alcohol solvent such as methanol, ethanol, propanol, t-butanol, etc. in the presence of an alcoholate like NaOMe, NaOEt, KO'Bu, etc. at 20-100° C. temperatures. The alcohol and the alcoholate should be matched. The use of co-solvent of toluene or xylene might be beneficial in order to control particle size of the product and to avoid gel formations. In a preferred embodiment catalytic amount of NaOMe is used in methanol or in methanol-toluene mixture at 40-60° C. (Zemplén deacylation). A further way to deacylate may be basic hydrolysis which generally means base catalyzed hydrolysis in water, alcohol or water-organic solvent mixtures, preferably water-methanol in homogeneous or heterogeneous reaction conditions at temperatures varying from 0-100° C. The base of choice is generally a strong base, e.g. LiOH, NaOH, KOH, $Ba(OH)_2$, $K_2CO_3$, basic ion exchange resins, tetraalkylammonium hydroxides, etc. The bases can be used in the form of an aqueous solution as well. In a preferred embodiment the base is NaOH and the solvent is methanol. An alternative way to deacylate may be aminolysis (N-acyl transfer based deprotection) which means a treatment with ammonia, hydrazine, substituted hydrazine, ethylene diamine or primary amines in water, alcohol or water-organic solvent mixtures at 20-120° C. temperatures. Under either conditions for deacylating mentioned above the acid labile protective groups or interglycosidic linkages are not affected.

The seventh aspect of the present application relates to the method for the preparation of 2'-O-fucosyllactose, characterized in that a compound of general formula 1

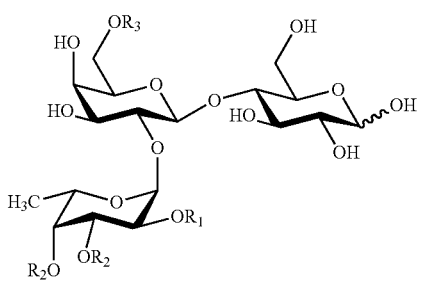

wherein $R_1$ and $R_2$, independently from each other, are a group removable by hydrogenolysis and $R_3$ is a group removable by hydrogenolysis or H—or a hydrate or solvate thereof is subjected to catalytic hydrogenolysis in a medium comprising water, or one or more $C_1$-$C_6$ alcohols, or mixtures thereof.

In one preferred embodiment 2'-O-fucosyllactose produced by methodologies of the present invention can be isolated as an amorphous solid by precipitation from water/organic solvent/aqueous solutions by cooling or by the addition of ethers including but not limited to MTBE, diethyl ether, diisopropyl ether etc. and/or $C_1$-$C_6$ alcohols. Alternatively 2'-O-fucosyllactose can also be isolated by freeze drying and spray drying.

In another preferred embodiment the hydrogenolysis of compounds characterized by general formula 1 is conducted using water or water-alcohol mixture as a solvent, 2-10% palladium on charcoal or palladium black as a catalyst in 1-10 atm of hydrogen pressure at 20-60° C. temperature. After the completion of the hydrogenolysis, the reaction mixture is filtered and preferably concentrated by removing the organic solvent components and subjected to precipitation, spray drying, freeze drying producing anhydrous and/or hydrated 2'-O-fucosyllactose (water content 0-20%) in a controlled manner.

In another preferred embodiment the hydrogenolysis of compounds characterized by general formula 1 is conducted using water or water-alcohol mixture as a solvent, 2-10% palladium on charcoal or palladium black as a catalyst in 1-10 atm hydrogen atmosphere pressure at 20-60° C. temperature. After the completion of the hydrogenolysis, the reaction mixture is filtered and preferably concentrated producing 2'-O-fucosyllactose aqueous solutions/syrup with a 2'-O-fucosyllactose concentration of 10-95%.

According to a preferred realization of the invention a compound of general formula 1, wherein $R_1$=$R_2$=benzyl and $R_3$ is H, in hydrated form or in a mixture of hydrated and crystalline water free forms is used in the hydrogenolysis.

In another preferred embodiment a compound of general formula 1, wherein $R_1$=$R_2$=benzyl and $R_3$ is H free from crystalline water is taken. Surprisingly, this anhydrous derivative shows excellent solubility in hot methanol (3 volumes) comparing to the dihydrate (which dissolves only partially in 10 volumes of hot methanol), allowing to carry out the reduction in less volume using less solvent(s). In addition, a simple, convenient and delicate removal of the solvent(s) can be applied affording 2'-FL in excellent yield and high purity.

Other features of the invention will become apparent in the course of the following descriptions of exemplary embodiments which are given for illustration of the invention and are not to be limiting thereof.

EXPERIMENTAL

Example 1

4-O-(3,4-O-cyclohexylidene-β-D-galactopyranosyl)-2,3:5,6-di-O-cyclohexylidene-D-glucose dimethyl acetal Lactose (1.15 g) is suspended in cyclohexanone dimethoxy ketal (10 ml). p-Toluene sulfonic acid (45 mg) is added and the reaction mixture is heated to 85° C. for 2½ h. The mixture is then neutralized by addition of $Et_3N$, the solvent is concentrated in vacuo, the residue is dissolved in DCM (60 ml), the organic phase is washed with $H_2O$ (2×50 ml) and sat. $NaHCO_3$ (50 ml). Further purification is done by flash chromatography (EtOAc/heptane 6:4) giving the product (1.35 g, 64%) as a white foam.

$^1$H NMR (300 MHz, $CDCl_3$): δ=4.54 (dd, 1H, J=6.6, 7.9), 4.42 (d, 1H, J=8.3), 4.35 (m, 1H), 4.34 (d, 1H, J=6.6), 4.26 (dd, 1H, J=5.3, 8.7), 4.09-3.92 (5H), 3.87 (dd, 1H, J=1.3, 7.9), 3.80 (m, 1H), 3.65 (m, 1H), 3.49 (m, 1H), 3.48 and 3.47 (2s, each 3H), 1.69-1.26 (m, 30H).

$^{13}$C NMR ($CDCl_3$, 75 MHz): δ=110.9, 110.3, 108.9, 107.2, 103.4, 79.0, 77.8, 77.5, 75.6, 75.1, 74.7, 74.4, 73.1, 63.9, 62.4, 57.4, 54.4, 37.8, 36.4, 35.8, 35.4, 34.9, 33.1, 25.2-23.6.

Example 2

4-O-(6-O-acetyl-3,4-O-cyclohexylidene-β-D-galactopyranosyl)-2,3:5,6-di-O-cyclohexylidene-D-glucose dimethyl acetal Compound of example 1 (0.526 g, 0.83 mmol) is dissolved in dry DCM (5 ml). Pyridine (0.4 ml, 5.0 mmol) is added and the mixture is cooled to −30° C. Acetyl chloride (0.07 ml, 0.98 mmol) dissolved in DCM (0.5 ml) is added in 10 min. The mixture is stirred for 1 h at −20° C. MeOH (1 ml) is added and the mixture is allowed to warm to room temperature. DCM (20 ml) is added and the mixture is washed with $H_2O$ (50 ml), cold aq. HCl (0.5 M, 30 ml), $H_2O$ (30 ml), $NaHCO_3$ (30 ml), then dried ($Na_2SO_4$), filtered and evaporated in vacuo. Purification by flash chromatography (heptane/EtOAc, 6:4) gives the product as a white foam (0.47 g, 85%).

$^1$H NMR ($CDCl_3$, 300 MHz) δ: 4.43-4.26 (6H, unresolved), 4.17 (1H, dd, J=7.1, 8.6), 4.13 (1H, dd, J=1.7, 1.7), 4.09-4.00 (3H, unresolved), 3.93 (1H, ddd, J=1.8, 4.6, 7.7), 3.85 (1H, dd, J=1.5, 7.5), 3.61 (1H, br s, OH), 3.51 (1H, dd, J=6.6, 8.3, H-2'), 3.42 (6H, s, 2×C$\underline{H}_3$O), 2.08 (3H, s, C$\underline{H}_3$CO), 1.81-1.25 (30H, unresolved, cyclohexyl).

$^{13}$C NMR ($CDCl_3$, 75 MHz) δ: 170.82 (CO), 110.9, 110.6, 108.9 (3×($CH_3$)$_2$$\underline{C}$), 105.3, 103.7 (C-1, C-1'), 78.5, 77.6, 77.6, 76.3, 74.7, 74.6, 72.8, 71.5 (C-2, C-3, C-4, C-5, C-2', C-3', C-4', C-5'), 64.3, 63.6 (C-6, C-6'), 56.1, 53.3 (2×$OCH_3$), 37.7-33.9, 25.1-23.6 (cyclohexyl).

Example 3

4-O-(6-O-trityl-3,4-O-isopropylidene-β-D-galactopyranosyl)-2,3:5,6-di-O-isopropylidene-D-glucose dimethyl acetal 3',4':2,3:5,6-Tri-O-isopropylidene-lactose dimethyl acetal (5.52 g, 10.9 mmol) is dissolved in dry pyridine (100 ml).

Trityl chloride (6.0 g, 21.5 mmol) is added together with DMAP (0.30 g) and the mixture is heated to 65° C. for 4 h. The mixture is evaporated in vacuo, coevaporated with toluene (3×30 ml). The residue is dissolved in EtOAc (50 ml), washed with $H_2O$ (50 ml), dried ($Na_2SO_4$), filtered and evaporated in vacuo. Purification by flash chromatography (hexane/EtOAc, 8:2, then 4:6) gives the product as an oil (3.0 g, 37%).

$^1$H NMR ($CDCl_3$, 500 MHz) δ: 7.45-7.22 (15H, 3×Ph), 4.38 (1H, d, J=8.5, H-1'), 4.38 (1H, m), 4.36 (1H, dd, J=6.5, 7.7), 4.27 (1H, d, J=6.1, H-1), 4.26 (1H, m), 4.14 (1H, dd, J=6.4, 8.8), 4.08 (1H, dd, J=5.6, 7.1), 4.00-3.97 (2H, unresolved), 3.85 (1H, dd, J=1.0, 7.6), 3.817 (1H, ddd, J=1.8, 5.3, 7.7), 3.56-3.52 (2H, unresolved), 3.25 (1H, dd, J=5.3, 8.5), 3.22 (3H, s, CH$_3$O), 3.09 (3H, s, CH$_3$O), 1.52, 1.50, 1.42, 1.34, 1.33, 1.32 (6×C(CH$_3$)$_2$).

$^{13}$C NMR ($CDCl_3$, 75 MHz) δ: 143.8, 128.6, 127.7, 127.0 (Ph), 110.1, 109.8, 108.2 (3×(CH$_3$)$_2$C), 104.5, 103.9 (C-1, C-1'), 86.7 (C(Ph)$_3$), 78.9, 77.9, 77.8, 76.1, 74.3, 74.2, 73.3, 72.5 (C-2, C-3, C-4, C-5, C-2', C-3', C-4', C-5'), 64.5, 62.0 (C-6, C-6'), 55.7, 52.2 (2×OMe), 28.2, 27.1, 26.3, 26.3, 25.5, 24.2 (6×C(CH$_3$)$_2$).

Example 4

4-O-(6-O-pivaloyl-3,4-O-isopropylidene-β-D-galactopyranosyl)-2,3:5,6-di-O-isopropylidene-D-glucose dimethyl acetal 3',4':2,3:5,6-Tri-O-isopropylidene-lactose dimethyl acetal (10 g, 19.7 mmol) was dissolved in DCM (80 ml) and pyridine (8 ml, 98.9 mmol) and cooled to 0° C. Pivaloyl chloride (8 ml, 39 mmol) was added dropwise and the mixture was stirred for 20 hours at room temperature. DCM (50 ml) was added and the mixture was washed with $H_2O$ (80 ml), aq. HCl (1M, 80 ml), $H_2O$ (80 ml), sat. $NaHCO_3$ (80 ml), dried ($Na_2SO_4$), filtered, evaporated and coevaporated with toluene. The residue was purified by flash chromatography (Hexane/EtOAc, 3:2) to give the product as a white foam (7.1 g, 61%).

$^1$H NMR ($CDCl_3$, 300 MHz) δ: 4.435 (1H, d, J=8.2, H-1'), 4.411 (1H, dd, J=6.0, 7.3, H-2), 4.361 (1H, d, J=6.03, H-1), 4.312 (1H, dd, J=6.8, 11.2, H-6'), 4.277 (1H, m), 4.243 (1H, dd, J=6.3, 11.1, H-6'), 4.173-4.034 (4H, unresolved), 3.997 (1H, dd, J=6.8, 8.8, H-6), 3.950 (1H, ddd, J=2.2, 6.3, 6.4), 3.905 (1H, dd, J=1.6, 7.3), 3.547 (1H, dd, J=7.1, 8.1, H-2'), 3.428, 3.416 (6H, 2×OMe), 1.500, 1.479, 1.374, 1.366, 1.318, 1.313 (6×3H, s, 6×C(CH$_3$)$_2$), 1.200 (9H, s, C(CH$_3$)$_3$).

$^{13}$C NMR ($CDCl_3$, 75 MHz) δ: 178.02 (CO), 110.11, 110.07, 108.19 (3×C(CH$_3$)$_2$), 104.99 (C-1), 103.44 (C-1'), 78.76, 77.79, 77.69, 75.93, 74.93, 74.07 (C-2'), 72.99, 64.53 (C-6'), 62.69 (C-6), 56.20, 53.05 (2×OCH$_3$), 38.62 (C(CH$_3$)$_3$), 28.02, 27.13, 27.01 (C(CH$_3$)$_3$), 26.34, 26.11, 25.55, 24.347 (6×CH$_3$).

Example 5

Compounds of general formula 5 were synthesized according to example 4 using the appropriate acylating agent.

a) 4-O-(6-O-(4-nitrobenzoyl)-3,4-O-isopropylidene-β-D-galactopyranosyl)-2,3:5,6-di-O-isopropylidene-D-glucose dimethyl acetal Yield: 98%, oil
$^1$H NMR ($CDCl_3$, 300 MHz): δ=8.30-8.23 (m, 4H), 4.65 (dd, 1H, J=4.5, 11.8), 4.58 (dd, 1H, J=7.3, 11.8), 4.44 (d, 1H, J=8.3), 4.42 (dd, 1H, J=6.2, 7.8), 4.27 (d, 1H, J=6.1), 4.27 (ddd, 1H, J=6.7, 6.7, 2.3), 4.18 (dd, 1H, J=5.5, 2.2), 4.16-4.10 (4H), 4.01 (dd, 1H, J=6.7, 8.8), 3.87 (dd, 1H, J=1.5, 7.8), 3.79 (s, 1H), 3.60 (dd, 1H, J=7.8, 7.8), 3.36, 3.35 (s, 2×3H), 1.52, 1.49, 1.36, 1.35, 1.34, 1.33 (s, 6×3H).

$^{13}$C NMR ($CDCl_3$, 75 MHz): δ=164.5, 150.6, 135.1, 131.0, 123.5, 110.5, 110.1, 108.3, 105.8, 103.9, 78.9, 77.8, 77.8, 76.6, 75.6, 74.2, 73.3, 71.4, 64.8, 64.7, 56.6, 54.3, 28.1, 27.2, 26.4, 26.3, 25.6, 24.7.

b) 4-O-(6-O-(4-phenylbenzoyl)-3,4-O-isopropylidene-β-D-galactopyranosyl)-2,3:5,6-di-O-isopropylidene-D-glucose dimethyl acetal Yield: 48%, colourless oil
$^1$H NMR ($CDCl_3$, 300 MHz) δ: 8.14-7.15 (9H, aromatic) 4.64 (1H, dd, J=4.9, 11.6, H-6a+), 4.55 (1H, dd, J=7.1, 11.6, H-6b'), 4.48 (1H, dd, J=5.9, 7.8, H-2), 4.48 (1H, d, J=8.1, H-1'), 4.27 (1H, d, J=6.1, H-1), 4.27 (1H, m), 4.22 (1H, dd, J=5.5, 2.3), 4.19-4.10 (4H, unresolved), 4.02 (1H, dd, J=6.8, 8.8, H-6b), 3.91 (1H, dd, J=1.5, 7.7, H-3), 3.63 (1H, s, OH), 3.61 (1H, dd, J=7.0, 6.9, H-2'), 3.35, 3.34 (2×3H, s, OCH$_3$), 1.54, 1.50, 1.40, 1.37, 1.36, 1.33 (6×3H, s, 6×C(CH$_3$)$_2$).

$^{13}$C NMR ($CDCl_3$, 75 MHz) δ: 166.2 (CO), 145.9, 139.8, 130.3-125.2 (aromatic C), 110.4, 110.1, 108.3 (3×C(CH$_3$)$_2$), 105.0, 103.7 (C-1, C-1'), 78.9, 77.8, 77.8, 76.4, 75.0, 74.2, 73.4, 71.6 (C-2, C-3, C-4, C-5, C-2', C-3', C-4', C-5'), 64.6, 64.0 (C-6, C-6'), 56.3, 53.2 (2×OCH$_3$), 28.1, 27.2, 26.4, 26.3, 25.6, 24.5 (6×CH$_3$).

c) 4-O-(6-O-propionyl-3,4-O-isopropylidene-β-D-galactopyranosyl)-2,3:5,6-di-O-isopropylidene-D-glucose dimethyl acetal Yield: 81%, colourless oil
$^1$H NMR ($CDCl_3$, 300 MHz): δ=4.42 (dd, 1H, J=6.2, 7.5), 4.40 (d, 1H, J=8.2), 4.35 (d, 1H, J=6.1), 4.32-4.24 (3H), 4.16-4.03 (4H), 3.99 (dd, 1H, J=6.8, 8.8), 3.93 (ddd, 1H, J=2.1, 5.2, 7.2), 3.88 (dd, 1H, J=1.6, 7.5, H-3), 3.54 (dd, 1H, J=8.0, 8.0, H-2'), 3.41, 3.41 (s, 2×3H), 2.34 (q, 2H), 1.49, 1.47, 1.37, 1.36, 1.31, 1.31 (s, 6×3H), 1.13 (t, 3H).

$^{13}$C NMR ($CDCl_3$, 75 MHz): δ=174.1, 110.3, 110.2, 108.3, 105.0, 103.6, 78.9, 77.9, 77.8, 76.3, 74.9, 74.1, 73.2, 71.4, 64.6, 63.2, 56.1, 53.0, 28.0, 27.3, 27.2, 26.3, 26.2, 25.6, 24.4, 8.95.

d) 4-O-(6-O-(4-chlorobenzoyl)-3,4-O-isopropylidene-β-D-galactopyranosyl)-2,3:5,6-di-O-isopropylidene-D-glucose dimethyl acetal White Foam
$^1$H NMR ($CDCl_3$): δ=8.10 and 7.42 (2 m, each 2H), 4.55 (2 ABq, each 1H, J=4.6, 7.4, 11.7), 4.45 (d, 1H, J=8.3), 4.43 (m, 1H), 4.27 (d, 1H, J=5.9), 4.11 (m, 2H), 3.37 and 3.34 (2 s, each 3H), 1.52, 1.48, 1.38, 1.36, 1.36 and 1.34 (6 s, each 3H).

$^{13}$C NMR ($CDCl_3$): δ=165.4, 139.6, 131.2, 128.7, 128.2, 110.4, 110.1, 108.3, 105.2, 103.8, 78.9, 77.8, 77.8, 76.5, 75.2, 74.2, 73.3, 71.5, 64.6, 64.2, 56.4, 53.5, 28.07, 27.2, 26.3, 26.2, 25.6, 24.6.

e) 4-O-(6-O-(4-phenylcarbamoyl-benzoyl)-3,4-O-isopropylidene-β-D-galactopyranosyl)-2,3:5,6-di-O-isopropylidene-D-glucose dimethyl acetal $^1$H-NMR (300 MHz, $CDCl_3$): δ=1.33 (s, 3H), 1.35 (s, 3H), 1.37 (s, 3H), 1.38 (s, 3H), 1.50 (s, 3H), 1.53 (s, 3H), 3.33 (s, 3H), 3.35 (s, 3H), 3.58-3.64 (m, 1H), 3.70 (d, 1H, J=1.1), 3.89 (dd, 1H, J=7.7, 1.4), 4.02 (dd, 1H, J=8.8, 6.8), 4.10-4.15 (m, 3H), 4.18-4.22 (m, 1H), 4.26-4.30 (m, 2H), 4.43-4.48 (m, 2H), 4.54-4.67 (m, 2H), 7.17 (t, 1H, J=7.4), 7.39 (t, 2H, J=7.6), 7.65 (d, 2H, J=7.6), 7.94 (d, 3H, J=8.5), 8.17 (d, 2H, J=8.4).

f) 4-O-(6-O-(4-(4-bromophenylcarbamoyl)-benzoyl)-3,4-O-isopropylidene-β-D-galactopyranosyl)-2,3:5,6-di-O-isopropylidene-D-glucose dimethyl acetal $^1$H-NMR (300 MHz, CDCl$_3$): δ=1.33 (s, 3H), 1.34 (s, 3H), 1.36 (s, 3H), 1.37 (s, 3H), 1.49 (s, 3H), 1.53 (s, 3H), 3.32 (s, 3H), 3.35 (s, 3H), 3.5 (d, 1H, J=4.5), 3.6 (t, 1H, J=7.9), 3.86-3.89 (m, 1H), 3.98-4.04 (m, 1H), 4.08-4.13 (m, 3H), 4.18-4.21 (m, 1H), 4.27-4.30 (m, 2H), 4.39-4.47 (m, 2H), 4.57-4.64 (m, 2H), 7.48 (d, 2H, J=8.8), 7.56 (d, 2H, J=8.8), 7.91 (d, 2H, J=8.3), 8.01 (s, 1H), 8.15 (d, 2H, J=8.3).

g) 4-O-(6-O-(4-benzamidobenzoyl)-3,4-O-isopropylidene-β-D-galactopyranosyl)-2,3:5,6-di-O-isopropylidene-D-glucose dimethyl acetal $^1$H-NMR (300 MHz, CDCl$_3$): δ=1.33 (s, 3H), 1.35 (s, 3H), 1.37 (s, 3H), 1.39 (s, 3H), 1.50 (s, 3H), 1.53 (s, 3H), 3.33 (s, 3H), 3.37 (s, 3H), 3.60 (t, 1H, J=7.8), 3.89 (dd, 1H, J=7.7, 1.4), 4.01 (dd, 1H, J=8.7, 6.8), 4.09-4.22 (m, 5H), 4.26-4.32 (m, 2H), 4.46-4.64 (m, 4H), 7.50-7.58 (m, 3H), 7.76 (d, 2H, J=8.7), 7.88 (d, 2H, J=7.9), 8.05 (s, 1H), 8.08 (d, 2H, J=8.7).

$^{13}$C-NMR (75 MHz, CDCl$_3$): δ=24.52, 25.63, 26.27, 26.38, 27.21, 28.11, 53.10, 56.34, 63.89, 64.64, 71.59, 73.37, 74.26, 74.99, 76.35, 77.85, 78.93, 103.73, 104.98, 108.27, 110.16, 110.38, 119.14, 125.37, 127.04, 128.90, 131.09, 132.26, 134.42, 142.36, 165.77.

h) 4-O-(6-O-(4-(4-nitrobenzamido)-benzoyl)-3,4-O-isopropylidene-β-D-galactopyranosyl)-2,3:5,6-di-O-isopropylidene-D-glucose dimethyl acetal $^1$H-NMR (300 MHz, CDCl$_3$): δ=1.33 (s, 3H), 1.34 (s, 3H), 1.37 (s, 3H), 1.38 (s, 3H), 1.49 (s, 3H), 1.51 (s, 3H), 3.33 (s, 3H), 3.37 (s, 3H), 3.60 (t, 1H, J=7.8 Hz), 3.89 (dd, 1H, J$^1$=7.7, 1.4 Hz), 4.01 (dd, 1H, J$^1$=8.7, 6.8 Hz), 4.08-4.26 (m, 5H), 4.26-4.37 (m, 2H), 4.40-4.63 (m, 4H), 7.77 (d, 2H, J=8.7 Hz), 8.04-8.09 (m, 4H), 8.31-8.34 (m, 3H).

$^{13}$C-NMR (75 MHz, CDCl$_3$): δ=24.47, 25.59, 26.23, 26.34, 27.18, 28.06, 53.09, 56.30, 63.98, 64.59, 71.51, 73.33, 74.27, 74.97, 76.35, 77.78, 77.87, 78.90, 103.67, 105.04, 108.26, 110.15, 110.38, 119.48, 123.98, 125.22, 126.01, 128.15, 128.39, 128.96, 131.08, 139.96, 141.72, 149.81, 163.82, 165.62.

i) 4-O-(6-O-(3,5-dinitrobenzoyl)-3,4-O-isopropylidene-β-D-galactopyranosyl)-2,3:5,6-di-O-isopropylidene-D-glucose dimethyl acetal Yield: 84%, pale yellow foam $^{13}$C NMR (CDCl$_3$): 162.57, 148.92 (two carbons), 133.83, 129.80 (two carbons), 122.64, 110.88, 110.37, 108.53, 106.05, 104.19, 79.26, 78.01, 77.82, 77.14, 76.10, 74.38, 73.49, 71.36, 65.71, 64.89, 57.09, 54.77, 28.32, 27.26, 26.55, 26.50, 25.93, 24.84.

j) 4-O-(6-O-(naphthalen-2-ylacetyl)-3,4-O-isopropylidene-β-D-galactopyranosyl)-2,3:5,6-di-O-isopropylidene-D-glucose dimethyl acetal Yield: 89%, white foam $^{13}$C NMR (CDCl$_3$): 171.48, 133.64, 132.70, 131.47, 128.52, 128.22, 127.88, 127.84, 127.45, 126.46, 126.13, 110.526, 110.50, 108.51, 105.53, 103.93, 79.14, 78.20, 78.07, 76.67, 75.47, 74.38, 73.30, 71.40, 64.84, 63.75, 56.47, 53.72, 41, 49, 28.30, 27.51, 26.64, 26.39, 25.88, 24.66.

Example 6

4-O-(6-O-(4-aminobenzoyl)-3,4-O-isopropylidene-β-D-galactopyranosyl)-2,3:5,6-di-O-isopropylidene-D-glucose dimethyl acetal Compound according to example 5a (400 mg, 608 μmol) is dissolved in 10 ml of THF and Pd/C (50 mg) is added. The suspension is stirred under H$_2$ atmosphere for three days until all starting material was consumed (TLC system: toluene-acetone 4:1 and 10% MeOH-DCM). The catalyst is filtrated over celite, and the residue is isolated by chromatography (5:1 toluene-acetone) as a white foam in 89% yield (341 mg).

$^{13}$C NMR (CDCl$_3$): 166.56, 151.12, 132.04 (two carbons), 119.51, 114.11 (two carbons), 110.55, 110.35, 108.51, 104.98, 103.98, 79.19, 78.07, 78.04, 76.55, 75.12, 74.53, 73.66, 71.94, 64.91, 63.59, 56.47, 53.12, 28.36, 27.44, 26.63, 26.51, 25.90, 24.75.

Example 7

Tetra-O-acetyl-L-fucose

Pyridine (295 ml, 3.65 mol) is cooled to 0° C. and L-Fucose (100 g, 609 mmol) is added during stirring. Ac$_2$O (287 ml, 3.04 mol) is added dropwise within 3 h. The reaction mixture is stirred for 2 h at 0° C. and for 24 h at room temperature. Methanol (25 ml, 618 mmol) is added dropwise and the reaction mixture is stirred for 30 min. The reaction mixture is then diluted with toluene (400 ml) and washed with water (3×300 ml). The aqueous phases are combined and extracted with toluene (300 ml). The organic phases are combined and washed with 1N HCl (3×500 ml), water (2×500 ml) and sat. NaHCO$_3$ solution (300 ml). The organic phase is dried and concentrated to dryness giving 197 g (98%) of product as a colourless syrup.

Example 8

Phenyl 2,3,4-tri-O-acetyl-1-thio-β-L-fucopyranoside

To a solution of compound of example 7 (196 g, 590 mmol) in toluene (200 ml) thiophenol (76 ml, 737 mmol) is added and the mixture is cooled to 0° C. BF$_3$Et$_2$O (112 ml, 885 mmol) is added dropwise in 60 min., then the reaction mixture is stirred for 3 h at 0° C., 12 h at 5° C. and 2 h at room temperature. The obtained mixture is washed with water (500 ml), water/brine (1:1) mixture (700 ml), 1N NaOH/brine (1:1) mixture (400 ml), water/brine (1:1) mixture (700 ml) and brine (300 ml). The combined and dried organic phases are evaporated to dryness at 70° C. to give 224 g of the title compound (99%).

Example 9

Phenyl 1-thio-β-L-fucopyranoside

Compound of example 8 (224 g) is dissolved in methanol (500 ml) and NaOMe (2 g, 37 mmol) is added. The reaction mixture is stirred at 40° C. for 2½ h. Methanol (250 ml) is distilled off and $CO_2$ is bubbled through the remaining solution for 5 min reaching pH=7. The reaction mixture is evaporated and isobutyl acetate (450 ml) is added. 50 ml of solvent is evaporated and the resulting mixture is subjected to crystallization by letting it at room temperature for 24 h. The white crystalline solid formed is filtered and washed with tert-butyl methyl ether (200 ml) giving 110 g (73%) of product after drying.

Example 10

Phenyl 3,4-O-isopropilidene-1-thio-β-L-fucopyranoside

Compound of example 9 (150 g, 0.58 mol) is suspended in 2,2-dimethoxypropane (550 ml, 4.5 mol) and a catalytic amount of p-TsOH (1.19 g, 6.2 mmol) is added. After stirring the mixture for 12 hours at room temperature $Et_3N$ (6 ml) is added slowly to neutralize the acid. The solution is evaporated to dryness (174 g), the residue is dissolved in diethyl ether (250 ml) and cooled to 0° C., then hexane (250 ml) is added dropwise to the mixture during vigorous stirring. The mixture is kept in fridge (5° C.) for 2 days and the precipitated white solid is filtrated and washed with hexane (200 ml) to give 145.48 g of compound (85%). the mother liquor is evaporated, the residue is dissolved in $Et_2O$ (25 ml) and hexane (25 ml) is added dropwise to it to crystallize 11.51 g of second crop. Combined yield: 91.5%. M.p.: 81° C., $[\alpha]_D=-28.15$ (1.03, MeOH).

Example 11

Phenyl 2,3,4-tri-O-benzyl-1-thio-β-L-fucopyranoside a) A solution of compound of example 9 (78 g) in DMF (70 ml) is added dropwise to a solution of NaH (54.6 g, 55-65% oily suspension) and benzyl bromide (159 ml) in DMF (400 ml) under cooling (0-5° C.). The reaction mixture is allowed to warm to room temperature, stirred for 4 hours, then cooled to 0° C. and methanol (94 ml) is added to it. The stirring is continued for 3 hours, the mixture is diluted with ethyl acetate (1 l) and washed with water (2×500 ml). The organic phase is separated and the product is crystallized by adding of methanol (1.2 l) and water (300 ml) to give white crystals (110 g). Physical characteristics are in good agreement with those reported [7].

b) A suspension of compound of example 9 (50 g) and tetrabutylammonium hydrogen sulphate (19.9 g) in DCM is warmed until a homogenous solution is obtained. To this solution benzyl chloride (101 ml) followed by 250 ml of 50% (w/w) NaOH-solution are added. The thick emulsion is refluxed under vigorous stirring. After 1.5 h 12 ml of MeOH is added and the reaction mixture is additionally refluxed for overnight. After cooling it is diluted with 200 ml of DCM and washed with water (400 ml) and brine (100 ml). DCM is evaporated to give a yellow oil (~150 g) to which 230 ml of MeOH is slowly added. The resulting suspension is stirred overnight at 4° C., the precipitate is filtered, washed with 200 ml of n-heptane and dried i.v. to yield 68 g of white powder. Physical characteristics are in good agreement with those reported [7].

Example 12

Phenyl 2,3,4-tri-O-(4-methylbenzyl)-1-thio-β-L-fucopyranoside 3.0 g (11.9 mmol) of compound of example 9 and 1.22 g (3.6 mmol, 0.3 eq.) tetrabutylammonium hydrogen sulphate is suspended in 20 ml of dichloromethane. The suspension is refluxed, under vigorous stirring, until a homogeneous solution is obtained. To this solution p-methylbenzyl chloride (7.23 ml, 53.6 mmol, 4.5 eq) followed by 5 ml of 50% (w/w) NaOH solution are added. The thick emulsion is refluxed for 3 hours while vigorously stirred, then 8 ml of MeOH are added and the reaction mixture is additionally refluxed for one night. After cooling DCM and water are added. The phases are separated and the aqueous phase is washed with DCM. The combined organic phases are washed with brine and the solvents are evaporated. The crude product is purified by column chromatography. The purest fractions are collected and the product is recrystallized from MeOH to yield 2.0 g of white solid. M.p.: 84-85° C.

$^{13}C$ NMR ($CDCl_3$): 137.60, 137.58, 137.31, 135.93, 135.63, 135.61, 134.76, 131.68, 129.33, 129.22, 129.04, 128.93, 128.71, 128.35, 127.94, 127.09, 87.85, 84.64, 77.45, 76.44, 75.65, 74.83, 74.54, 72.98, 21.45, 17.55.

Example 13

Phenyl 2,3,4-tri-O-(2,4,6-trimethylbenzyl)-1-thio-β-L-fucopyranoside

A dry 250 ml flask is filled with 6.6 g (152 mmol) of sodium hydride in mineral oil emulsion (55%). Dry dimethylformamide (10 ml) is added and the mixture is cooled to 0° C. To this mixture bromomethylmesitylene (32.4 g, 152 mmol) in dry DMF (20 ml) is added. Compound of example 9 (10 g, 39 mmol) is dissolved in dry DMF (20 mL) and added very to the above mixture over 40 minutes. After an additional hour the ice-bath is removed and the reaction is stirred at room temperature for 21 hours. Methanol (15 ml) is added to quench and the reaction mixture is stirred for another hour, then it is diluted with ethyl acetate (200 ml) and extracted with sat. $NaHCO_3$ (200 ml), 1N HCl (200 ml), water (200 ml) and brine (200 ml). The title compound is obtained after column chromatography purification and crystallization.

$^1$H-NMR (300 MHz, $CDCl_3$): δ=1.33 (d, 3H, J=5.7 Hz), 2.25 (s, 6H), 2.28 (s, 9H), 2.29 (s, 3H), 2.33 (s, 3H), 2.37 (s, 6H), 3.52-3.59 (m, 3H), 3.93 (t, 1H, J=8.9 Hz), 4.45 (dd, 2H, J=9.9 Hz, J=16 Hz), 4.53-4.57 (m, 2H), 4.85 (d, 1H, J=11.3 Hz), 5.02 (d, 1H, J=9.8 Hz), 5.16 (d, 1H, J=13.7 Hz), 6.80 (d, 4H, J=4.5 Hz), 6.89 (s, 2H), 7.04-7.18 (m, 3H), 7.51 (d, 2H, J=8.2 Hz).

$^{13}$C-NMR (75 MHz, $CDCl_3$): δ=17.36, 19.67, 19.79, 20.95, 20.97, 21.0, 67.31, 68.89, 69.82, 74.43, 77.39, 77.95, 85.39, 87.49, 126.45, 128.52, 128.59, 128.65, 128.86, 130.68, 131.66, 131.86, 132.10, 134.59, 137.14, 137.34, 137.36, 137.82, 137.99, 138.01.

Example 14

Phenyl 2,3,4-tri-O-(2,3,4,5,6-tetramethylbenzyl)-1-thio-β-L-fucopyranoside

A dry 250 ml flask is filled with 7.2 g (164 mmol) sodium hydride as mineral oil emulsion (55%). Pentamethylbenzyl bromide (39.6 g, 164 mmol) was dissolved in dry DMF (90 ml) and added to the sodium hydride. The mixture is cooled to 0° C. with ice-bath and compound of example 9 (10 g, 39 mmol) in dry DMF (60 ml) is added. A heavy precipitate occurs after full addition. The reaction mixture is diluted with 50 ml of THF and heated to 70° C. for 13 hours.

Methanol (50 ml) is then added and the mixture is poured into methanol (400 ml) under heavy stirring. The mixture is filtered, washed with methanol, water, methanol/water 1:1 and twice methanol. The solid is dried on the oil-pump. Weight: 26.9 g (94% yield).

$^1$H-NMR (300 MHz, CDCl$_3$): δ=1.36 (d, 3H, J=6.3 Hz), 2.15 (s, 3H), 2.16 (s, 3H), 2.17 (s, 6H), 2.19 (s, 6H), 2.22 (s, 3H), 2.23 (s, 3H), 2.26 (s, 3H), 2.27 (s, 6H), 2.31 (s, 3H), 2.35 (s, 9H), 3.61-3.65 (m, 3H), 4.00 (t, 1H, J=9.2 Hz), 4.46-4.70 (m, 4H), 5.00 (d, 1H, J=11.5 Hz), 5.09 (d, 1H, J=10.2 Hz), 5.34 (d, 1H, J=9.5 Hz), 6.97-7.14 (m, 3H), 7.50-7.53 (m, 2H).

$^{13}$C-NMR (75 MHz, CDCl$_3$): δ=16.26, 16.48, 16.55, 16.62, 16.69, 16.97, 16.99, 17.01, 17.51, 67.43, 68.46, 69.82, 71.07, 74.42, 77.28, 77.57, 85.87, 87.57, 126.34, 128.46, 130.73, 131.56, 131.98, 132.02, 132.17, 132.27, 132.35, 133.46, 133.66, 133.82, 134.43, 134.68, 134.72.

Example 15

Typical glycosylation procedure to obtain compounds of general formula 2 or 2' wherein R$_4$ or R'$_4$ mean a group removable by hydrogenolysis, optionally substituted acyl, acetal type group or silyl Donor 4 (1.2 eq. to acceptor) is dissolved in 3-5 volumes of DCM and cooled with ice-bath. To the cold solution bromine (0.5-1.2 eq. to donor) is added at 0-5° C. After 5 minutes cyclohexene (0.5-1.5 eq. to Br$_2$) is then added until color becomes slightly yellow. A pre-prepared solution of acceptor 5 and TBAB (10 mol % to acceptor) in DMF (1.4-2.1 volumes to acceptor) is added dropwise to the donor and the reaction mixture is stirred under ice-cooling until the ice thaws and afterwards at room temperature for overall 24-72 hours. Triethyl amine (0.5-1 eq. to Br$_2$) is added and the resulting suspension is diluted with diisopropyl ether, t-butyl dimethyl ether or toluene (5-15 volumes to theoretical yield) and extracted twice with sat. NaHCO$_3$ (3-10 volumes to theoretical yield), once with 1 N HCl (3-10 volumes to theoretical yield), twice with sat. NaHCO$_3$ (3-10 volumes to theoretical yield) and once with brine (3-10 volumes to theoretical yield). The organic layer is concentrated in vacuo to furnish the crude product which is then purified by crystallization, precipitation or column chromatography. Yields range between 65-80% (calculated on the acceptor).

a) O-(2,3,4-tri-O-benzyl-α-L-fucopyranosyl)-(1→2)-O-(6-O-(4-chlorobenzoyl)-3,4-isopropylidene-β-D-galactopyranosyl)-(1→4)-2,3:5,6-di-O-isopropylidene-D-glucose dimethyl acetal $^1$H NMR (CDCl$_3$): δ=8.00, 7.45-7.25 (2 m, 19H), 5.61 (d, 1H, J=3.1), 4.99 and 4.66 (ABq, 2H, J=11.6), 4.89 and 4.75 (ABq, 2H, J=11.9), 4.75 (s, 2H), 4.71 (d, 1H, J=8.0), 4.54 (m, 2H), 4.51 (dd, 1H, J=6.1, 7.6), 4.35 (d, 1H), 4.25 (m, 1H), 4.19 (m, 1H), 4.12 (m, 1H), 4.07 and 3.90 (2 m, each 1H), 4.05 (m, 5H), 3.73 (dd, 1H), 3.65 (br s, 1H), 3.47 and 3.34 (2 s, each 3H), 1.49, 1.43, 1.37, 1.37, 1.31 and 1.27 (6 s, each 3H), 1.12 (d, 1H, J=6.5).

$^{13}$C NMR (CDCl$_3$): δ=165.3, 110.3, 109.9, 108.5, 105.1, 101.1, 95.1, 80.1, 79.1, 77.9, 77.6, 77.4, 76.3, 75.2, 74.9, 74.1, 73.6, 70.7, 66.3, 74.7, 73.0, 72.5, 65.0, 63.9, 56.0, 52.8, 27.8, 27.2, 26.7, 26.7, 26.4, 25.1, 16.8.

b) O-(2,3,4-tri-O-benzyl-α-L-fucopyranosyl)-(1→2)-O-(6-O-benzoyl-3,4-isopropylidene-β-D-galactopyranosyl)-(1→4)-2,3:5,6-di-O-isopropylidene-D-glucose dimethyl acetal $^1$H NMR (CDCl$_3$): δ=8.08 and 7.60-7.25 (2 m, 20H), 5.63 (d, 1H, J=3.1), 5.00 and 4.66 (ABq, 2H, J=11.6), 4.89 and 4.75 (ABq, 2H, J=11.9), 4.77 (s, 2H), 4.72 (d, 1H, J=8.0), 4.55 (m, 2H), 4.50 (dd, 1H), 4.36 (d, 1H), 4.24 (m, 1H), 4.23 (m, 1H), 4.19 (m, 1H), 4.08 and 3.90 (2 m, each 1H), 4.05 (m, 5H), 3.76 (dd, 1H), 3.66 (br s, 1H), 3.37 and 3.34 (2 s, each 3H), 1.50, 1.44, 1.37, 1.37, 1.34 and 1.28 (6 s, each 3H), 1.12 (d, 1H, J=6.5).

$^{13}$C NMR (CDCl$_3$): δ=166.2, 110.3, 109.9, 108.6, 105.0, 101.2, 95.1, 81.0, 79.1, 77.9, 77.6, 77.4, 76.3, 75.2, 74.7, 74.0, 73.7, 70.5, 66.3, 74.8, 73.0, 72.5, 65.0, 63.7, 56.0, 52.7, 27.8, 27.1, 26.8, 26.7, 26.4, 25.1, 16.8.

c) O-(2,3,4-tri-O-benzyl-α-L-fucopyranosyl)-(1→2)-O-(6-O-(4-nitrobenzoyl)-3,4-isopropylidene-β-D-galactopyranosyl)-(1→4)-2,3:5,6-di-O-isopropylidene-D-glucose dimethyl acetal $^1$H NMR (CDCl$_3$): δ=8.25 and 7.45-7.25 (2 m, 19H), 5.60 (d, 1H, J=3.2), 5.00 and 4.66 (ABq, 2H, J=11.6), 4.88 and 4.75 (ABq, 2H, J=12.0), 4.76 (s, 2H), 4.69 (d, 1H, J=8.4), 4.60 (m, 2H), 4.50 (dd, 1H, J=6.2, 7.5), 4.34 (d, 1H), 4.24 (m, 1H), 4.17 (m, 1H), 4.11 (m, 1H), 4.08 and 3.96 (2 m, each 1H), 4.05 (m, 5H), 3.76 (dd, 1H), 3.68 (br s, 1H), 3.38 and 3.34 (2 s, each 3H), 1.49, 1.43, 1.37, 1.37, 1.33 and 1.27 (6 s, each 3H), 1.11 (d, 1H, J=6.5).

$^{13}$C NMR (CDCl$_3$): δ=164.6, 110.7, 110.3 and 108.9, 105.8, 101.5, 95.5, 80.4, 79.4, 78.2, 77.9, 77.7, 76.6, 75.4, 75.4, 74.5, 73.9, 70.9, 66.7, 75.0, 73.3, 72.9, 65.3, 64.8, 56.5, 53.5, 28.6, 27.5, 27.1, 27.1, 26.7, 25.4, 17.1.

d) O-(2,3,4-tri-O-benzyl-α-L-fucopyranosyl)-(1→2)-O-(6-O-(4-phenylbenzoyl)-3,4-isopropylidene-β-D-galactopyranosyl)-(1→4)-2,3:5,6-di-O-isopropylidene-D-glucose dimethyl acetal $^1$H NMR (CDCl$_3$): δ=8.12, 7.70-7.60 and 7.50-7.25 (3 m, 24H), 5.62 (d, 1H, J=3.1), 5.00 and 4.65 (ABq, 2H, J=11.6), 4.89 and 4.75 (ABq, 2H, J=11.8), 4.77 (s, 2H), 4.72 (d, 1H, J=7.9), 4.58 (m, 2H), 4.54 (dd, 1H, J=5.9, 7.6), 4.37 (d, 1H), 4.27 (m, 1H), 4.24 (m, 1H), 4.21 (m, 1H), 4.09 and 3.89 (2 m, each 1H), 4.17-3.99 (m, 6H), 3.77 (dd, 1H), 3.68 (br s, 1H), 3.39 and 3.36 (2 s, each 3H), 1.51, 1.44, 1.38, 1.38, 1.35 and 1.27 (6 s, each 3H), 1.11 (d, 1H, J=6.48).

$^{13}$C NMR (CDCl$_3$): δ=166.1, 110.3, 109.9, 108.6, 105.0, 101.2, 95.1, 80.1, 79.1, 77.9, 77.6, 77.4, 76.4, 75.3, 74.7, 74.0, 73.7, 70.8, 66.4, 74.8, 73.1, 72.6, 65.1, 64.7, 56.0, 52.8, 27.8, 27.2, 26.8, 26.8, 26.5, 25.2, 16.8.

e) O-(2,3,4-tri-O-benzyl-α-L-fucopyranosyl)-(1→2)-O-(6-O-(4-methoxybenzoyl)-3,4-isopropylidene-β-D-galactopyranosyl)-(1→4)-2,3:5,6-di-O-isopropylidene-D-glucose dimethyl acetal $^1$H NMR (CDCl$_3$): δ=8.01, 7.45-7.25 and 6.93 (3 m, 19H), 5.61 (d, 1H, J=2.9), 4.99 and 4.66 (ABq, 2H, J=11.6), 4.89 and 4.71 (ABq, 2H, J=11.9), 4.76 (s, 2H), 4.71 (d, 1H, J=8.0), 4.52 (m, 3H), 4.36 (d, 1H), 4.25 (m, 1H), 4.20 (m, 1H), 4.15-3.98 (m, 6H), 4.08 and 3.88 (2 m, each 1H), 3.83 (s, 3H), 3.76 (dd, 1H), 3.68 (br s, 1H), 3.38 and 3.35 (2 s, each 3H), 1.50, 1.44, 1.37, 1.37, 1.33 and 1.27 (6 s, each 3H), 1.11 (d, 1H, J=6.5).

$^{13}$C NMR (CDCl$_3$): δ=166.3, 110.5, 110.2, 108.9, 105.4, 101.4, 95.5, 80.5, 79.5, 78.2, 77.9, 76.9, 75.5, 75.2, 74.2, 73.9, 72.9, 71.2, 66.9, 74.9, 73.2, 72.9, 65.3, 63.6, 56.3, 55.7, 52.9, 28.1, 27.1, 27.0, 27.0, 26.8, 25.4, 16.8.

f) O-(2,3,4-tri-O-benzyl-α-L-fucopyranosyl)-(1→2)-O-(6-O-(4-tert-butylbenzoyl)-3,4-isopropylidene-β-D-galactopyranosyl)-(1→4)-2,3:5,6-di-O-isopropylidene-D-glucose dimethyl acetal $^1$H NMR (CDCl$_3$): δ=8.00 and 7.50-7.25 (2 m, 19H), 5.63 (d, 1H, J=2.9), 5.00 and 4.67 (ABq, 2H, J=11.6), 4.90 and 4.74 (ABq, 2H, J=11.9), 4.77 (s, 2H), 4.72 (d, 1H, J=8.2), 4.58 (m, 3H), 4.36 (d, 1H), 4.24 (m, 1H), 4.21 (m, 1H), 4.16-3.99 (m, 6H), 4.06 and 3.89 (2 m, each 1H), 3.76 (dd, 1H), 3.66 (br s, 1H), 3.39 and 3.35 (2 s, each 3H), 1.51, 1.45, 1.38, 1.38, 1.35, 1.35, 1.35, 1.35 and 1.27 (9 s, each 3H), 1.13 (d, 1H, J=6.5).
$^{13}$C NMR (CDCl$_3$): δ=166.5, 110.5, 110.2, 108.9, 105.2, 101.5, 95.4, 80.4, 79.4, 78.2, 77.9, 77.8, 76.7, 75.5, 75.1, 74.3, 73.9, 71.1, 66.6, 75.0, 73.4, 72.8, 66.6, 63.4, 56.2, 53.10, 35.3, 31.3, 28.1, 27.5, 27.1, 27.1, 26.7, 25.4, 17.1.

g) O-(2,3,4-tri-O-benzyl-α-L-fucopyranosyl)-(1→2)-O-(6-O-trifluoroacetyl-3,4-isopropylidene-β-D-galactopyranosyl)-(1→4)-2,3:5,6-di-O-isopropylidene-D-glucose dimethyl acetal $^1$H NMR (CDCl$_3$): δ=7.40-7.25 (m, 15H), 5.55 (d, 1H, J=3.2), 4.97 and 4.59 (ABq, 2H, J=11.8), 4.86 and 4.74 (ABq, 2H, J=11.3), 4.75 (s, 2H), 4.70 (d, 1H, J=8.3), 4.55 (m, 2H), 4.42 (m, 1H), 4.33 (d, 1H), 4.22-3.99 (m, 8H), 4.06 and 3.86 (2 m, each 1H), 3.71 (dd, 1H), 3.65 (br s, 1H), 3.42 and 3.42 (2 s, each 3H), 1.50, 1.40, 1.37, 1.37, 1.35 and 1.25 (6 s, each 3H), 1.09 (d, 1H, J=6.5).
$^{13}$C NMR (CDCl$_3$): δ=165.7, 110.6, 110.2, 108.8, 105.2, 101.2, 95.2, 79.9, 79.4, 78.4, 78.0, 77.9, 76.2, 75.9, 75.1, 74.3, 73.9, 71.1, 66.3, 75.0, 73.5, 72.5, 66.6, 63.4, 56.2, 53.1, 28.1, 27.2, 27.1, 27.1, 26.7, 25.4, 16.4.

h) O-(2,3,4-tri-O-benzyl-α-L-fucopyranosyl)-(1→2)-O-(6-O-trichloroacetyl-3,4-isopropylidene-β-D-galactopyranosyl)-(1→4)-2,3:5,6-di-O-isopropylidene-D-glucose dimethyl acetal $^1$H NMR (CDCl$_3$): δ=7.45-7.25 (m, 15H), 5.58 (d, 1H, J=3.2), 5.00 and 4.65 (ABq, 2H, J=11.6), 4.87 and 4.75 (ABq, 2H, J=11.9), 4.76 (s, 2H), 4.70 (d, 1H, J=8.0), 4.55 (m, 2H), 4.46 (dd, 1H, J=6.0, 7.6), 4.36 (d, 1H), 4.23-3.97 (m, 8H), 4.04 and 3.97 (2 m, each 1H), 3.74 (dd, 1H), 3.67 (br s, 1H), 3.44 and 3.44 (2 s, each 3H), 1.49, 1.43, 1.38, 1.36, 1.31 and 1.28 (6 s, each 3H), 1.11 (d, 1H, J=6.5).
$^{13}$C NMR (CDCl$_3$): δ=164.4, 110.7, 110.1, 108.9, 105.2, 101.5, 95.2, 79.9, 79.3, 77.9, 77.7, 76.7, 75.3, 74.9, 73.9, 73.3, 73.0, 70.0, 66.36, 76.4, 74.7, 73.3, 66.7, 65.0, 56.4, 53.4, 27.9, 27.2, 26.9, 26.5, 25.2, 25.1, 16.6.

i) O-(2,3,4-tri-O-benzyl-α-L-fucopyranosyl)-(1→2)-O-(6-O-dichloroacetyl-3,4-isopropylidene-β-D-galactopyranosyl)-(1→4)-2,3:5,6-di-O-isopropylidene-D-glucose dimethyl acetal $^1$H NMR (CDCl$_3$): δ=7.45-7.25 (m, 15H), 6.12 (s, 1H), 5.57 (d, 1H, J=3.6), 4.98 and 4.65 (ABq, 2H, J=11.6), 4.88 and 4.70 (ABq, 2H, J=11.9), 4.76 (s, 2H), 4.60 (d, 1H, J=8.1), 4.46 (m, 3H), 4.3 (d, 1H), 4.20-3.86 (m, 8H), 4.08 and 3.84 (2 m, each 1H), 3.71 (dd, 1H), 3.65 (br s, 1H), 3.47 and 3.45 (2 s, each 3H), 1.46, 1.42, 1.37, 1.36, 1.31 and 1.28 (6 s, each 3H), 1.10 (d, 1H, J=6.5).
$^{13}$C NMR (CDCl$_3$): δ=164.7, 110.7, 110.4, 109.0, 106.6, 101.6, 95.5, 80.3, 79.3, 78.1, 77.8, 77.4, 76.6, 75.9, 75.3, 75.2, 73.2, 70.4, 66.6, 75.9, 73.3, 72.9, 65.9, 65.4, 64.4, 56.7, 54.7, 28.0, 27.6, 27.1, 27.0, 26.7, 25.4, 17.1.

j) O-(2,3,4-tri-O-benzyl-α-L-fucopyranosyl)-(1→2)-O-(6-O-trityl-3,4-isopropylidene-β-D-galactopyranosyl)-(1→4)-2,3:5,6-di-O-isopropylidene-D-glucose dimethyl acetal $^1$H NMR (CDCl$_3$): δ=7.50-7.20 (m, 30H), 5.65 (d, 1H, J=3.4), 5.00 and 4.65 (ABq, 2H, J=11.6), 4.90 and 4.75 (ABq, 2H, J=11.9), 4.8 (ABq, 2H, J=11.8), 4.53 (d, 1H, J=8.2), 4.42 (dd, 1H), 4.32 (dd, 1H), 4.26 (d, 1H, J=5.3, 4.19-3.63 (m, 11H), 4.03 and 3.84 (2 m, each 1H), 3.58 (dd, 1H), 3.10 and 3.05 (2 s, each 3H), 1.49, 1.44, 1.43, 1.33, 1.30 and 1.27 (6 s, each 3H), 1.09 (d, 1H, J=6.5).
$^{13}$C NMR (CDCl$_3$): δ=110.1, 110.0, 108.9, 105.1, 101.8, 95.8, 80.6, 79.4, 78.2, 77.9, 77.3, 76.6, 75.6, 74.2, 74.1, 73.9, 71.9, 66.4, 74.9, 73.4, 72.7, 66.5, 61.7, 55.8, 52.3, 28.3, 27.4, 27.1, 26.9, 26.8, 25.5, 17.1.

k) O-(2,3,4-tri-O-benzyl-α-L-fucopyranosyl)-(1→2)-O-(6-O-chloroacetyl-3,4-isopropylidene-β-D-galactopyranosyl)-(1→4)-2,3:5,6-di-O-isopropylidene-D-glucose dimethyl acetal $^1$H NMR (CDCl$_3$): δ=7.43-7.25 (m, 15H), 5.58 (d, 1H, J=3.5), 4.98 and 4.65 (ABq, 2H, J=11.6), 4.88 and 4.74 (ABq, 2H, J=11.9), 4.74 (s, 2H), 4.61 (d, 1H, J=8.1), 4.45 (m, 3H), 4.32 (d, 1H), 4.25-3.85 (m, 8H), 4.13 (d, 2H), 3.72 (dd, 1H), 3.66 (br s, 1H), 3.44 and 3.43 (2 s, each 3H), 1.47, 1.43, 1.37, 1.36, 1.32 and 1.28 (6 s, each 3H), 1.10 (d, 1H, J=6.5).
$^{13}$C NMR (CDCl$_3$): δ=167.1, 110.3, 110.0, 108.6, 105.9, 101.1, 95.1, 80.1, 79.0, 77.8, 77.5, 77.2, 76.2, 75.4, 75.0, 74.6, 73.4, 70.3, 66.3, 74.7, 73.0, 72.5, 65.1, 64.7, 56.2, 53.8, 40.7, 28.7, 27.3, 26.8, 26.7, 26.4, 25.1, 16.7.

l) O-(2,3,4-tri-O-(3-phenylbenzyl)-α-L-fucopyranosyl)-(1→2)-O-(6-O-pivaloyl-3,4-isopropylidene-β-D-galactopyranosyl)-(1→4)-2,3:5,6-di-O-isopropylidene-D-glucose dimethyl acetal $^1$H NMR (CDCl$_3$, 300 MHz): δ=7.68-7.26 (27H), 5.66 (d, 1H, J=2.4), 5.10 and 4.78 (ABq, 2H, J=11.4), 5.03 and 4.87 (ABq, 2H, J=11.7), 4.87 (s, 2H), 4.80 (d, 1H, J=8.1), 4.50 (dd, 1H, J=6.0, 7.5), 4.39 (d, 1H, J=6.0), 4.29-4.01 (m, 11H), 3.95 (dd, 1H, J=6.6, 8.4), 3.86 (m, 1H), 3.80 (br s, 1H), 3.75 (dd, 1H, J=6.6, 8.1), 3.45, 3.44 (s, 2×3H), 1.49, 1.46, 1.39, 1.38, 1.27, 1.27 (6×s, each 3H), 1.23 (s, 9H), 1.15 (d, 3H, J=6.5).
$^{13}$C NMR (CDCl$_3$, 75 MHz): δ=177.9, 141.2-126.0, 110.1, 109.8, 108.5, 105.0, 101.2, 94.9, 80.1, 79.2, 78.3, 77.6, 77.5, 76.6, 75.1, 74.9, 74.7, 73.8, 73.3, 73.2, 72.6, 70.2, 66.3, 65.0, 62.2, 56.0, 52.7, 38.7, 27.8-25.1, 16.9.

m) O-(2,3,4-tri-O-benzyl-α-L-fucopyranosyl)-(1→2)-O-(6-O-pivaloyl-3,4-isopropylidene-β-D-galactopyranosyl)-(1→4)-2,3:5,6-di-O-isopropylidene-D-glucose dimethyl acetal $^1$H NMR (CDCl$_3$): δ=7.45-7.25 (m, 15H), 5.60 (d, 1H, J=3.2), 4.98 and 4.65 (ABq, 2H, J=11.6), 4.88 and 4.74 (ABq, 2H, J=11.9), 4.76 (s, 2H), 4.65 (d, 1H, J=8.2), 4.48 (dd, 1H, J=6.0, 7.4), 4.38 (d, 1H), 4.29 (m, 2H), 4.24 (m, 1H), 4.19 (m, 1H), 4.08 (m, 2H), 4.08 and 3.88 (2 m, each 1H), 4.06 (m, 2H), 3.98 and 3.91 (2 m, each 1H) 3.72 (dd, 1H), 3.66 (br s, 1H), 3.43 (2 s, each 3H), 1.48, 1.42, 1.37, 1.36, 1.31 and 1.28 (6 s, each 3H), 1.21 (s, 9H), 1.10 (d, 1H, J=6.5).

¹³C NMR (CDCl₃): δ=178.2, 110.4, 110.1, 108.8, 105.3, 101.6, 95.3, 80.4, 79.4, 78.2, 77.8, 77.8, 76.6, 75.6, 74.2, 72.8, 72.8, 70.6, 66.6, 75.0, 73.6, 73.4, 65.3, 62.6, 56.3, 53.0, 39.0, 28.1, 27.5, 27.4, 27.4, 27.3, 27.1, 27.0, 26.6, 24.6, 17.1.

n) O-(2,3,4-tri-O-(4-methylbenzyl)-α-L-fucopyranosyl)-(1→2)-O-(6-O-pivaloyl-3,4-isopropylidene-β-D-galactopyranosyl)-(1→4)-2,3:5,6-di-O-isopropylidene-D-glucose dimethyl acetal ¹H-NMR (300 MHz, CDCl₃): δ=1.09 (d, 3H, J=6.4 Hz), 1.24 (s, 9H), 1.30 (s, 3H), 1.34 (s, 3H), 1.37 (s, 3H), 1.40 (s, 3H), 1.45 (s, 3H), 1.50 (s, 3H), 2.35-2.37 (m, 9H), 3.44 (s, 6H), 3.62-3.64 (m, 1H), 3.73 (t, 1H, J=7.3 Hz), 3.89-4.30 (m, 13H), 4.39 (d, 1H, J=6.0 Hz), 4.48-4.51 (m, 1H), 4.62-4.73 (m, 5H), 4.85 (d, 1H, J=11.6 Hz), 4.95 (d, 1H, J=11.6 Hz), 5.56 (d, 1H, J=3.4 Hz), 7.12-7.33 (m, 12H).

¹³C-NMR (75 MHz, CDCl₃): δ=16.74, 21.08, 25.13, 26.29, 26.66, 26.77, 26.99, 27.10, 27.13, 27.71, 38.61, 52.58, 55.91, 62.28, 65.00, 66.27, 70.25, 72.40, 72.91, 73.23, 73.98, 74.28, 74.58, 75.24, 76.13, 77.20, 77.30, 77.51, 78.97, 79.95, 95.11, 101.27, 104.95, 108.47, 109.78, 109.99, 127.39, 127.64, 128.40, 128.65, 128.68, 128.85, 135.68, 135.96, 136.18, 136.67, 136.75, 136.88, 177.87.

o) O-(2,3,4-tri-O-(naphtalen-2-ylmethyl)-α-L-fucopyranosyl)-(1→2)-O-(6-O-pivaloyl-3,4-isopropylidene-β-D-galactopyranosyl)-(1→4)-2,3:5,6-di-O-isopropylidene-D-glucose dimethyl acetal ¹H NMR (CDCl₃, 300 MHz): δ=7.87-7.42 (21H), 5.70 (d, 1H, J=3.3), 5.15 and 4.89 (ABq, 2H, J=12.0), 5.10 and 4.94 (ABq, 2H, J=12.3), 4.96 (s, 2H), 4.68 (d, 1H, J=8.1), 4.48 (dd, 1H, J=6.0, 7.2), 4.37 (d, 1H, J=6.0), 4.28-3.71 (m, 16H), 3.43, 3.42 (2×s, each 3H), 1.50, 1.47, 1.36, 1.34, 1.31, 1.23 (6×s, each 3H), 1.22 (s, 9H), 1.34 (d, 3H, J=6.3).

¹³C NMR (CDCl₃, 75 MHz): δ=178.0, 136.8-125.8, 110.1, 109.9, 108.5, 104.9, 101.3, 94.8, 80.1, 79.3, 77.9, 77.7, 77.6, 75.1, 74.8, 74.7, 73.7, 73.3, 72.9, 72.9, 72.6, 70.3, 66.4, 64.9, 62.3, 56.0, 52.7, 38.7, 27.8, 27.1, 26.8, 26.7, 26.4, 25.1, 27.1, 16.9.

p) O-(2,3,4-tri-O-(4-chlorobenzyl)-α-L-fucopyranosyl)-(1→2)-O-(6-O-pivaloyl-3,4-isopropylidene-β-D-galactopyranosyl)-(1→4)-2,3:5,6-di-O-isopropylidene-D-glucose dimethyl acetal ¹H NMR (CDCl₃, 300 MHz): δ=7.31-7.25 (12H), 5.59 (d, 1H, J=3.0), 4.87 and 4.59 (ABq, 2H, J=11.7), 4.79 and 4.66 (ABq, 2H, J=12.3), 4.68 (s, 2H), 4.66 (d, 1H, J=8.4), 4.46 (dd, 1H, J=5.9, 7.5), 4.37 (d, 1H, J=5.9), 4.29-3.90 (m, 16H), 3.70 (dd, 1H, J=6.3, 8.1), 3.63 (br s, 1H), 3.44, 3.43 (2×s, each 3H), 1.48, 1.42, 1.38, 1.36, 1.31, 1.28 (6×s, each 3H), 1.21 (s, 9H), 1.13 (d, 3H, J=6.5).

¹³C NMR (CDCl₃, 75 MHz): δ=177.9, 137.6-128.2, 110.1, 109.8, 108.4, 105.0, 101.1, 94.7, 80.2, 78.8, 78.5, 77.6, 77.6, 76.4, 75.1, 74.8, 74.1, 73.7, 73.4, 72.2, 71.6, 70.3, 66.2, 64.9, 62.3, 56.1, 52.9, 38.7, 27.8, 27.1, 26.8, 26.7, 26.4, 25.0, 27.0, 16.8.

q) O-(2,3,4-tri-O-(3-phenylbenzyl)-α-L-fucopyranosyl)-(1→2)-O-(6-O-benzoyl-3,4-isopropylidene-β-D-galactopyranosyl)-(1→4)-2,3:5,6-di-O-isopropylidene-D-glucose dimethyl acetal ¹H NMR (CDCl₃, 300 MHz): δ 8.14-7.25 (m, 32H), 5.67 (d, 1H, J=1.7 Hz), 5.10 (d, 1H, J=11.6 Hz), 5.03 (d, 1H, J=12.0 Hz), 4.89-4.85 (m, 3H), 4.78 (d, 1H, J=11.6 Hz), 4.74 (d, 1H, J=8.0 Hz), 4.60-4.51 (m, 3H), 4.37 (d, 1H, J=5.9 Hz), 4.30 (m, 1H), 4.24-3.94 (m, 10H), 3.80 (s, 1H), 3.78 (dd, 1H, J=7.2 Hz), 3.38, 3.35 (2×s, each 3H), 1.50, 1.47, 1.39, 1.39, 1.29, 1.27 (6×s, each 3H), 1.19 (d, 3H, J=6.4 Hz)

¹³C NMR (CDCl₃, 75.4 MHz): δ 166.2, 141.2-126.4, 110.3, 109.9, 108.6, 105.0, 101.2, 95.0, 80.1, 79.3, 78.3, 77.7, 77.6, 76.7, 75.1, 74.9, 74.9, 73.9, 73.7, 73.2, 72.7, 70.7, 66.4, 65.1, 63.7, 56.0, 52.8, 27.8, 27.2, 26.8, 26.8, 26.4, 25.1, 16.9.

r) O-(2,3,4-tri-O-(4-chlorobenzyl)-α-L-fucopyranosyl)-(1→2)-O-(6-O-benzoyl-3,4-isopropylidene-β-D-galactopyranosyl)-(1→4)-2,3:5,6-di-O-isopropylidene-D-glucose dimethyl acetal ¹H NMR (CDCl₃, 300 MHz): δ=8.20-7.32 (m, 17H), 5.67 (d, 1H, J=3 Hz), 4.94 (d, 1H, J=11.7 Hz), 4.85 (d, 1H, J=12.1 Hz), 4.79-4.59 (m, 7H), 4.56 (dd, 1H, J=6.0, 7.5 Hz), 4.42 (d, 1H, J=5.9 Hz), 4.34 (m, 1H), 4.26-4.03 (m, 9H), 3.98 (1H, dd, J=6.7, 8.3 Hz), 3.80 (1H, d, J=5.8, 7.8 Hz), 3.70 (1H, br s), 3.44, 3.42 (2×s, each 3H), 1.56, 1.49, 1.44, 1.44, 1.40, 1.34 (6×s, each 3H), 1.20 (d, 3H)

¹³C NMR (CDCl₃, 75 MHz): δ=166.3, 137.6-128.3, 110.4, 109.9, 108.6, 105.0, 101.1, 94.8, 80.3, 78.9, 78.5, 77.6, 76.4, 75.2, 75.0, 74.2, 73.8, 73.8, 72.3, 71.7, 70.8, 66.3, 65.0, 63.6, 56.1, 52.9, 27.9, 27.1, 26.8, 26.7, 26.5, 25.0, 16.8.

s) O-(2,3,4-tri-O-benzyl-α-L-fucopyranosyl)-(1→2)-O-(6-O-(4-benzamidobenzoyl)-3,4-isopropylidene-β-D-galactopyranosyl)-(1→4)-2,3:5,6-di-O-isopropylidene-D-glucose dimethyl acetal ¹H-NMR (CDCl₃, 300 MHz): δ=1.11 (d, 3H, J=6.4), 1.28 (s, 3H), 1.34 (s, 3H), 1.37 (s, 6H), 1.44 (s, 3H), 1.50 (s, 3H), 3.36 (s, 3H), 3.38 (s, 3H), 3.68 (br s, 1H), 3.76 (t, 1H, J=7.2), 3.87-3.93 (m, 1H), 4.01-4.10 (m, 7H), 4.16-4.29 (m, 3H), 4.36 (d, 1H, J=5.9), 4.51-4.55 (m, 3H), 4.68-4.76 (m, 5H), 4.89 (d, 1H, J=11.9), 4.99 (d, 1H, J=11.6), 5.61 (d, 1H, J=2.9), 7.26-7.42 (m, 15H), 7.47-7.59 (m, 3H), 7.77 (d, 2H, J=8.6), 7.88 (d, 2H, J=7.3), 8.06 (d, 2H, J=8.6), 8.09 (s, 1H).

¹³C-NMR (CDCl₃, 75 MHz): δ=17.1, 25.4, 26.7, 27.0, 27.1, 27.5, 28.1, 53.0, 56.4, 63.9, 65.3, 66.6, 71.1, 72.8, 73.4, 74.0, 74.3, 75.0, 75.1, 75.5, 76.6, 77.5, 77.9, 78.2, 79.4, 80.4, 95.4, 101.5, 105.3, 108.9, 110.2, 110.6, 119.4, 125.7, 127.3, 127.53, 127.57, 127.63, 127.7, 127.9, 128.4, 128.5, 128.6, 129.2, 131.3, 132.5, 134.7, 139.0, 139.2, 139.5, 142.6, 166.0, 166.1.

t) O-(2,3,4-tri-O-(2,4,6-trimethylbenzyl)-α-L-fucopyranosyl)-(1→2)-O-(6-O-pivaloyl-3,4-isopropylidene-β-D-galactopyranosyl)-(1→4)-2,3:5,6-di-O-isopropylidene-D-glucose dimethyl acetal ¹H NMR (300 MHz, CDCl₃): δ=1.19 (d, 3H, J=6.5 Hz), 1.23 (s, 9H), 1.26 (s, 3H), 1.29 (s, 3H), 1.41 (s, 6H), 1.45 (s, 3H), 1.47 (s, 3H), 2.21 (s, 3H), 2.23 (s, 15H), 2.26 (s, 3H), 2.33 (s, 6H), 3.44 (s, 3H), 3.35 (s, 3H), 3.62 (bs, 1H), 3.73 (dd, 1H, J=5.6 Hz, J=7.7 Hz), 3.91-4.15 (m, 10H), 4.26-4.35 (m, 4H), 4.38-4.40 (m, 1H), 4.47-4.52 (m, 2H), 4.62-4.66 (m, 2H), 4.73-4.82 (m, 2H), 5.03 (d, 1H, J=9.4 Hz), 5.56 (d, 1H, J=3.0 Hz), 6.75 (s, 2H), 6.76 (s, 2H), 6.80 (s, 2H).

¹³C-NMR (75 MHz, CDCl₃): δ=178.06, 138.30, 137.81, 137.60, 137.14, 136.96, 136.91, 132.31, 132.21, 131.98, 128.62, 128.48, 110.12, 109.81, 108.61, 105.02, 101.55, 94.59, 79.95, 79.52, 78.73, 78.38, 77.59, 74.69, 74.24, 74.13, 73.31, 70.32, 69.30, 68.27, 66.45, 66.44, 65.11, 62.40, 56.07, 52.77, 50.17, 38.72, 27.74, 27.10, 26.95, 26.89, 26.28, 25.27, 22.67, 20.97, 20.94, 20.92, 19.68, 19.57, 19.51, 16.86.

u) O-(2,3,4-tri-O-(2,4,6-trimethylbenzyl-α-L-fucopyranosyl)-(1→2)-O-(6-O-(4-benzamidobenzoyl)-3,4-isopropylidene-β-D-galactopyranosyl)-(1→4)-2, 3:5,6-di-O-isopropylidene-D-glucose dimethyl acetal $^1$H-NMR (300 MHz, CDCl$_3$): δ=1.21 (d, 3H, J=6.4 Hz), 1.27 (s, 3H), 1.29 (s, 3H), 1.41 (s, 3H), 1.42 (s, 3H), 1.47 (s, 3H), 1.49 (s, 3H), 2.21 (s, 3H), 2.22 (s, 3H), 2.24 (s, 12H), 2.25 (s, 3H), 2.33 (s, 6H), 3.39 (s, 3H), 3.40 (s, 3H), 3.63 (bs, 1H), 3.77 (dd, 1H, J=6.7 Hz, J=7.5 Hz), 3.98-4.17 (m, 10H), 4.27-4.40 (m, 3H), 4.47-4.57 (m, 4H), 4.63-4.83 (m, 4H), 5.04 (d, 1H, J=9.3 Hz), 5.58 (d, 1H, J=2.9 Hz), 6.75 (s, 2H), 6.76 (s, 2H), 6.80 (s, 2H), 7.49-7.62 (m, 3H), 7.78 (d, 2H, J=8.7 Hz), 7.89 (d, 2H, J=7.0 Hz), 8.02 (bs, 1H), 8.09 (d, 2H, J=8.6 Hz).

$^{13}$C-NMR (75 MHz, CDCl$_3$): δ=165.75, 142.33, 138.30, 137.81, 137.58, 137.14, 136.98, 136.91, 134.39, 132.31, 131.98, 131.03, 128.92, 128.63, 128.48, 127.03, 125.49, 119.14, 110.30, 109.86, 108.64, 105.04, 101.48, 94.61, 79.96, 79.51, 78.71, 78.39, 77.63, 74.82, 74.32, 74.10, 73.68, 70.75, 68.26, 66.47, 66.43, 65.14, 63.64, 56.13, 52.83, 31.85, 27.74, 27.17, 26.95, 26.90, 26.37, 25.25, 22.67, 20.94, 20.92, 19.68, 19.57, 19.51, 16.87, 14.10.

v) O-(2,3,4-tri-O-(2,3,4,5,6-pentamethylbenzyl-α-L-fucopyranosyl)-(1→2)-O-(6-O-(4-benzamidobenzoyl)-3,4-isopropylidene-β-D-galactopyranosyl)-(1→4)-2,3:5,6-di-O-isopropylidene-D-glucose dimethyl acetal $^1$H-NMR (300 MHz, CDCl$_3$): δ=1.23 (d, 3H, J=6.3 Hz), 1.28 (s, 6H), 1.42 (s, 3H), 1.44 (s, 3H), 1.47 (s, 3H), 1.49 (s, 3H), 2.16 (s, 12H), 2.20 (s, 18H), 2.24 (s, 3H), 2.25 (s, 6H), 2.29 (s, 6H), 3.39 (s, 3H), 3.41 (s, 3H), 3.72 (bs, 1H), 3.77-3.81 (m, 1H), 4.01-4.21 (m, 10H), 4.28-4.32 (m, 1H), 4.39-4.43 (m, 2H), 4.54-4.59 (m, 4H), 4.72-4.79 (m, 3H), 4.88 (d, 1H, J=10.7 Hz), 5.23 (d, 1H, J=9.5 Hz), 5.58 (d, 1H, J=3.0 Hz), 7.50-7.63 (m, 3H), 7.78 (d, 2H, J=8.1 Hz), 7.90 (d, 2H, J=8.2 Hz), 8.03 (bs, 1H), 8.10 (d, 2H, J=8.1 Hz).

Example 16

General deacylation method of compounds of general formula 2 or 2' wherein R$_4$ or R'$_4$ is optionally substituted acyl to obtain compounds of general formula 2 or 2' wherein R$_4$ or R'$_4$ is H A 6'-O-acyl compound according to example 15 (1.0 eq.) is dissolved in MeOH and to which NaOMe (1.5 eq.) is added at room temperature. The mixture is stirred between room temperature and 40° C. for 3 hours to overnight. The base is then neutralized with Amberlite IR 120 (H$^+$) ion exchange resin and filtered off. The filtrate is concentrated and the crude product is purified by either crystallization or flash chromatography (hexane/EtOAc) to give compounds of general formula 2 or 2' wherein R$_4$ or R'$_4$ is H.

According to an alternative method the starting material is dissolved in a mixture of MeOH and DCM. NaOMe (1.5 eq.) is added at room temperature, the mixture is stirred between room temperature and 40° C. for 3 hours to overnight. The base is then neutralized with Amberlite IR 120 (H$^+$) ion exchange resin and filtered off. DCM and brine is added to the filtrate and the phases are separated. The organic phase is dried, filtered and concentrated in vacuo.

Yields range between 60 and 80%.

a) O-(2,3,4-tri-O-(3-phenylbenzyl)-α-L-fucopyranosyl)-(1→2)-O-(3,4-isopropylidene-β-D-galactopyranosyl)-(1→4)-2,3:5,6-di-O-isopropylidene-D-glucose dimethyl acetal $^1$H NMR (CDCl$_3$, 300 MHz): δ=7.70-7.31 (27H), 5.12 and 4.80 (ABq, 2H, J=11.4), 5.05 and 4.89 (ABq, 2H, J=12.0), 4.88 (s, 2H), 4.66 (dd, 1H, J=7.2, 7.8), 4.60 (d, 1H, J=8.1), 4.39 (d, 1H, J=6.9), 4.29 (m, 1H), 4.22 (dd, 1H, J=5.7, 6.3), 4.19-3.64 (14H), 3.52 (s, 2×3H), 1.49, 1.49, 1.42, 1.41, 1.29, 1.28 (s, 6×3H), 1.20 (d, 3H, J=6.6).

$^{13}$C NMR (CDCl$_3$, 75 MHz): δ=141.2-125.9, 110.4, 109.7, 108.6, 107.5, 101.4, 95.0, 80.7, 79.2, 78.3, 77.9, 77.3, 76.6, 75.4, 74.9, 74.8, 74.4, 74.2, 73.9, 73.1, 72.6, 66.3, 64.9, 62.4, 57.7, 53.9, 27.9, 27.1, 26.9, 26.6, 26.4, 25.0, 16.9.

b) O-(2,3,4-tri-O-(4-methylbenzyl)-α-L-fucopyranosyl)-(1→2)-O-(3,4-isopropylidene-β-D-galactopyranosyl)-(1→4)-2,3:5,6-di-O-isopropylidene-D-glucose dimethyl acetal $^1$H-NMR (300 MHz, CDCl$_3$): δ=1.07 (d, 3H, J=6.4 Hz), 1.30 (s, 3H), 1.32 (s, 3H), 1.37 (s, 3H), 1.39 (s, 3H), 1.44 (s, 3H), 1.46 (s, 3H), 2.34 (s, 6H), 2.36 (s, 3H), 3.50 (s, 6H), 3.60-3.72 (m, 4H), 3.77-3.85 (m, 2H), 3.90-4.08 (m, 8H), 4.20-4.24 (m, 2H), 4.36 (d, 1H, J=7.0 Hz), 4.53 (d, 1H, J=8.2 Hz), 4.60-4.73 (m, 5H), 4.84 (d, 1H, J=11.7 Hz), 4.94 (d, 1H, J=11.6 Hz), 5.54 (d, 1H, J=3.6 Hz), 7.10-7.17 (m, 6H), 7.22-7.25 (m, 2H), 7.28-7.32 (m, 4H).

$^{13}$C-NMR (75 MHz, CDCl$_3$): δ=136.96, 136.86, 136.81, 136.16, 135.89, 135.72, 128.92, 128.76, 128.71, 128.43, 127.76, 127.44, 110.38, 109.63, 108.73, 107.56, 101.42, 95.31, 80.67, 78.96, 77.83, 77.46, 76.07, 75.65, 74.70, 74.46, 74.41, 74.30, 73.84, 72.90, 72.49, 66.25, 65.03, 62.41, 57.67, 54.00, 27.84, 27.08, 26.95, 26.50, 26.45, 25.12, 21.14, 16.80.

c) O-(2,3,4-tri-O-(2-naphtylmethyl)-α-L-fucopyranosyl)-(1→2)-O-(3,4-isopropylidene-β-D-galactopyranosyl)-(1→4)-2,3:5,6-di-O-isopropylidene-D-glucose dimethyl acetal $^1$H NMR (CDCl$_3$, 300 MHz): δ=7.87-7.41 (21H), 5.69 (d, 1H, J=3.3), 5.15 and 4.89 (ABq, 2H, J=12.0), 5.11 and 4.95 (ABq, 2H, J=11.4), 4.97 (s, 2H), 4.63 (dd, 1H, J=7.0, 7.8), 4.59 (d, 1H, J=8.4), 4.36 (d, 1H, J=6.9), 4.25-3.65 (16H), 3.50 (s, 2×3H), 1.48, 1.48, 1.38, 1.36, 1.31, 1.22 (s, 6×3H), 1.14 (d, 3H, J=6.3).

$^{13}$C NMR (CDCl$_3$, 75 MHz): δ=136.8-125.7, 110.5, 109.7, 108.7, 107.5, 101.4, 95.0, 80.7, 79.3, 78.0, 77.9, 76.6, 75.5, 74.8, 74.4, 74.2, 73.9, 73.3, 72.7, 66.4, 64.9, 62.4, 57.7, 53.9, 27.9, 27.1, 26.9, 26.6, 26.5, 25.0, 16.9.

d) O-(2,3,4-tri-O-(4-chlorobenzyl)-α-L-fucopyranosyl)-(1→2)-O-(3,4-isopropylidene-β-D-galactopyranosyl)-(1→4)-2,3:5,6-di-O-isopropylidene-D-glucose dimethyl acetal $^1$H NMR (CDCl$_3$, 300 MHz): δ=7.28-7.24 (12H), 5.56 (d, 1H, J=3.0), 4.86 (d, 1H, J=11.7), 4.78 (d, 1H, J=12.1), 4.72-4.53 (6H), 4.35 (d, 1H, J=6.9), 4.24 (m, 1H), 4.16-3.80 (4H), 3.69 (dd, 1H, J=6.9, 8.2), 3.64-3.60 (m, 3H), 3.49 (s, 2×3H), 1.46, 1.42, 1.38, 1.36, 1.29, 1.28 (s, 6×3H), 1.11 (d, 3H, J=6.6).

$^{13}$C NMR (CDCl$_3$, 75 MHz): δ=137.6-128.3, 110.5, 109.7, 108.6, 107.5, 101.3, 94.9, 80.7, 78.7, 78.5, 77.9, 77.4, 76.3, 75.4, 74.9, 74.5, 74.1, 74.1, 73.9, 72.2, 71.7, 66.2, 64.8, 62.4, 57.7, 54.0, 27.9, 27.0, 26.8, 26.6, 26.5, 25.0.

e) O-(2,3,4-tri-O-benzyl-α-L-fucopyranosyl)-(1→2)-O-(3,4-isopropylidene-β-D-galacto-pyranosyl)-(1→4)-2,3:5,6-di-O-isopropylidene-D-glucose dimethyl acetal amorphous white solid $^1$H-NMR (300 MHz, CDCl$_3$): δ=1.10 (d, 3H, J=6.5 Hz), 1.29 (s, 3H), 1.31 (s, 3H), 1.37 (s, 3H), 1.39 (s, 3H), 1.44 (s, 3H), 1.46 (s, 3H), 3.62-3.85 (m, 6H), 3.90-4.09 (m, 8H), 4.19-4.25 (m, 2H), 4.36 (d, 1H, J=7.0 Hz), 4.55 (d, 1H, J=8.2 Hz), 4.61-4.77 (m, 4H), 4.88 (d, 1H, J=12.0 Hz), 4.98 (d, 1H, J=11.6 Hz), 5.58 (d, 1H, J=3.4 Hz), 7.26-7.42 (m, 15H).
$^{13}$C-NMR (75 MHz, CDCl$_3$): δ=139.15, 138.87, 138.72, 128.29, 128.25, 128.08, 128.07, 127.65, 127.39, 127.33, 127.27, 110.41, 109.65, 108.72, 107.56, 101.38, 95.16, 80.68, 78.98, 77.95, 77.86, 77.14, 76.26, 75.58, 74.76, 74.69, 74.43, 74.31, 73.87, 73.00, 72.55, 66.25, 64.95, 62.39, 57.69, 54.04, 27.86, 27.06, 26.90, 26.54, 26.45, 25.09, 16.80.

Example 17

O-(2,3,4-tri-O-benzyl-α-L-fucopyranosyl)-(1→2)-O-β-D-galactopyranosyl-(1→4)-D-glucose Mixture of Dihydrate and Anhydrate a) Compound of example 16e (2.3 g) is dissolved in 75% acetic acid (15 ml) and kept in 75° C. for 6 hours. The reaction mixture is concentrated, taken up in ethyl acetate (15 ml), washed with sat. NaHCO$_3$ solution and brine. The organic phase is cooled to 4° C. under slow stirring and the product crystallizes giving 1.0 g of a white solid (55%).

b) Compound of example 16e (2.3 g) is dissolved in ethyl acetate/CH$_3$CN/water 4:4:1 mixture (15 ml) and pTsOH monohydrate is added (0.15 eq). The reaction mixture is stirred for 20 hours at 35° C. The product crystallizes out from the reaction mixture affording 1.1 g of a white solid (62%).

c) Compound of example 16e (2.3 g) is dissolved in THF/1M HCl 2:1 mixture (15 ml) and stirred for 44 hours at 35° C. The product crystallizes out from the reaction mixture affording 1.1 g of a white solid (62%).

d) Donor 4 (example 11, 10.0 g) is dissolved in 40 ml of DCM and cooled with ice-bath. To the cold solution bromine (0.5 ml) is added at 0-5° C. After 5 minutes cyclohexene (0.5 ml) is then added until color becomes slightly yellow. A pre-prepared solution of the crude acceptor 5 (example 5 g, 11.6 g, 81% purity) and TBAB (10 mol % to acceptor) in DMF (20 ml) is added dropwise to the donor and the reaction mixture is stirred under ice-cooling until the ice thaws and afterwards at room temperature for 38 hours. The reaction mixture is diluted with toluene (150 ml) and extracted 3 times with sat. NaHCO$_3$ (100 ml), once with 1 N HCl (100 ml), 3 times with sat. NaHCO$_3$ (100 ml) and once with brine (100 ml). The organic layer is concentrated in vacuo to furnish a yellow-orange oil which is dissolved in TBME (35 ml). The trisaccharide is precipitated by addition of heptane (255 ml) giving rise to 15.4 g of white powder which is dissolved in MeOH (60 ml). To this solution a mixture of NaOH/MeOH (0.32 g in 15 ml) is added dropwise. After 18 hours the white solid is filtered off and the solution is diluted with toluene (150 ml). The organic phase is washed with 1 M HCl (150 ml), NaHCO$_3$ (150 ml) and H$_2$O/brine 4:1 (150 ml) followed by evaporation of the solvent and drying overnight. The crude product is dissolved in MeCN/EtOAc/H$_2$O (75 ml) and pTsOH monohydrate (0.6 g) is added. After stirring for 19 h at 40° C. the mixture is diluted with EtOAc (75 ml) and washed with NaHCO$_3$ (sat.) (90 ml) and brine (90 ml). The combined aqueous phase is re-washed twice with EtOAc (2×20 ml). The combined organic phase is slowly stirred at 4° C. overnight and the white crystals are filtered off to give the desired trisaccharide (5.34 g, 45% based on the acceptor).

Example 18

O-(2,3,4-tri-O-benzyl-α-L-fucopyranosyl)-(1→2)-O-β-D-galactopyranosyl-(1→4)-D-glucose (Free from Crystalline Water)

a) Compound according to example 17 (8 g) is dissolved in 7 ml of DMSO and diluted with ethyl acetate (30 ml). This organic solution is washed with water (2×30 ml). White crystals precipitate from the organic phase upon standing which are collected affording 7.05 g of product. Purity by HPLC: 98.1%.

b) To the solution of compound according to example 11 in DCM (2000 ml) 73 ml of bromine in DCM (200 ml) are added at 5-10° C. After 10 min cyclohexene (130 ml) is added at the same temperature. A solution of compound of example 4 (600 g) and TBAB (25 g) in DMF (1200 ml) is dropped to the above solution under cooling. The reaction mixture is stirred at rt for 48 hours, then it is diluted with toluene (20 l) and washed with sat NaHCO$_3$ and water (each 30 l). The organic phase is concentrated to give 17 l of yellow oil, which is dissolved in methanol (1.8 l) and 120 g of NaOMe are added and the mixture is stirred at rt for 18 hours. After neutralization with Amberlite IR 120 H$^+$ (600 g) the resin is filtered off and the filtrate is concentrated at reduced pressure affording cca. 1 l of yellow semisolid material, which is taken up in 60% aq. acetic acid (2.5 l) and the solution is stirred at 65° C. for 3 days. The solvents are evaporated and the remaining material is dissolved in ethyl acetate (3 l), the solution is extracted with water (2×4 l), the water phase is back-extracted with ethyl acetate (500 ml). The combined organic phases are stored in freezer for 2 days. The white solid formed is filtered, washed with cold ethyl acetate and recrystallized from methanol (750 ml) to yield 210 g of white crystalline compound.

$^1$H-NMR (200 MHz, DMSO-d$_6$) (mixture of α/β) δ: 1.05 (m, 3H), 2.98 (m, 1H), 3.10-3.90 (m, 13H), 4.05-5.00 (m, 16H), 5.54 (br s, 1H), 6.38 (d, 0.6H), 6.72 (d, 0.4H), 7.05-7.20 (m, 15H).

IR spectrum exhibits characteristic peaks at 3375, 2929, 1462, 1454, 1402, 1384, 1078, 1044 cm$^{-1}$ (see FIG. 2).

X-Ray Powder Diffraction

XRPD investigations were conducted with a Philips PW 1830/PW1050 instrument in transmission geometry, using CuKα radiation made monochromatic by means of a graphite monochromator. D-spacings are calculated from the 2θ values, based on a wavelength of 1.54186 Å. As a general rule the 2θ values have an error rate of ±0.2 Å. FIG. 1 shows the pattern and the table below contains the list of peaks.

| 2Θ | rel. |
| --- | --- |
| 4.58 | 77 |
| 8.44 | 18 |
| 10.6 | 33 |
| 12.8 | 25 |
| 13.3 | 36 |
| 13.9 | 20 |
| 14.2 | 34 |
| 16.9 | 81 |
| 17.4 | 56 |

-continued

| 2Θ | rel. |
|---|---|
| 19.1 | 22 |
| 19.7 | 7 |
| 20.4 | 19 |
| 20.9 | 100 |
| 21.4 | 38 |
| 22.2 | 14 |
| 23.4 | 12 |
| 23.8 | 23 |
| 24.3 | 16 |
| 24.8 | 11 |
| 24.9 | 12 |
| 25.8 | 12 |
| 25.9 | 9 |
| 26.5 | 9 |
| 26.9 | 13 |
| 27.4 | 6 |
| 28.0 | 3 |
| 28.9 | 5 |
| 29.7 | 8 |
| 31.0 | 5 |

DSC Analysis

The measurement was carried out on a SETARAM labsys Evo TG-DSC thermoanalyzer, in flowing high purity (6.0) Helium atmosphere (flow rate 20 ml/min), in the temperature range of 30-300° C. with a constant heating rate of 10 K/min, using standard 100 μl platinum crucible. 10.4 mg of sample was weighted. The thermogram is shown in FIG. 3.

Example 19

O-(2,3,4-tri-O-(4-methylbenzyl)-α-L-fucopyranosyl)-(1→2)-O-β-D-galactopyranosyl-(1→4)-D-glucose Compound of example 16b (0.28 g, 0.29 mmol) is dissolved in 60% acetic acid (5 ml) and stirred at 50° C. for 70 hours. The mixture is concentrated in vacuo, taken up in EtOAc (20 ml) and extracted with sat. NaHCO$_3$ (10 ml), water (10 ml) and brine (10 ml). After drying over MgSO$_4$, the mixture is concentrated in vacuo and the remaining residue was crystallized from EtOAc/heptane to give rise to a white crystalline solid, mp: 112-117° C.

$^1$H-NMR (300 MHz, CDCl$_3$/d$_4$-MeOH 5:3): δ=1.06 (d, 3H, J=5.1 Hz), 2.30 (s, 6H), 2.33 (s, 3H), 3.18-3.25 (m, 1H), 3.43-3.87 (m, 14H), 3.87-4.06 (m, 2H), 4.18-4.42 (m, 1H), 4.45 (d, 0.5H, J=7.8 Hz), 4.68-4.74 (m, 4H), 4.85 (d, 1H, J=11.3 Hz), 5.10 (d, 0.5H, J=3.6 Hz), 5.25 (d, 0.5H, J=3.6 Hz), 5.29 (d, 0.5H, J=3.6 Hz), 7.07-7.19 (m, 8H), 7.22-7.27 (m, 4H).

Example 20

2'-O-fucosyllactose a) A suspension of compound according to example 18 (10.0 g) in a mixture of methanol/isopropanol/acetic acid (100 ml: 50 ml: 5 ml) is heated gently to get a clear solution to which a suspension of 10% Pd on charcoal (1.0 g) in water (10 ml) is added. The mixture is stirred at room temperature for 12 hours under hydrogen atmosphere (6 bar). The catalyst is filtered, the filtrate is concentrated and the product is precipitated by addition of MTBE (25 ml) to give 6.6 g of white amorphous solid. Purity by HPLC: 99.7%.

HPLC-MS: ESI+ 511.2 [M+Na]$^+$, 527.2 [M+K]$^+$; ESI– 487.4 [M–H]$^-$, 523.2 [M+Cl]$^-$, 577.3 [M$_2$+H]$^-$.

$^1$H-NMR (600 MHz, D$_2$O) δ: α-D-glucose H-1 5.22 d, H-2 3.59 dd, H-3* 3.80 dd, H-4 3.71 dd, H-5 3.91 m, H-6×3.90 m, H-6y 3.80 m; β-D-glucose H-1 4.63 d, H-2 3.29 dd, H-3 3.58 dd, H-4 3.72 dd, H-5 3.47 ddd, H-6×3.94 dd, H-6y 3.76 dd; D-galactose H-1 4.52 d, H-2 3.66 dd, H-3 3.88 m, H-4 3.90 m, H-5 3.81 m, H-6×3.81 m, H-6y 3.74 m; L-fucose H-1 5.30 d, H-2*3.80 m, H-3*3.80 m, H-4 3.82 d, H-5 4.22, 4.25 qd, CH$_3$ 1.22 d.

$^{13}$C-NMR (150 MHz, D$_2$O) δ: α-D-glucose C-1 94.5, C-2 74.0, C-3* 72.3, C-4 77.9, C-5 73.1, C-6 62.7; (3-D-glucose C-1 98.6, C-2 76.6, C-3 77.0, C-4 78.5, C-5 78.0, C-6 62.9; D-galactose C-1 102.9, C-2 79.0, C-3 76.3, C-4 71.9, C-5 74.0, C-6 63.8; L-fucose C-1 102.0, C-2* 72.4, C-3* 70.9, C-4 74.4, C-5 69.6, CH$_3$ 18.0. (* interchangeable assignments)

b) To a suspension of compound according to example 17 (100 g) in methanol (1000 ml) 10% Pd on charcoal (8.3 g) is added. The mixture is stirred at 35° C. for 5 hours under hydrogen atmosphere (5 atm). The catalyst is filtered off, the filtrate is concentrated and the product is precipitated to give 61.8 g of white amorphous solid.

LIST OF REFERENCES

1. S. A. Abbas, J. J. Barlow, K. L. Matta, *Carbohydr. Res.* 1981, 88, 51-60.
2. A. Fernandez-Mayoralas, M. Martin-Lomas, *Carbohydr. Res.* 1986, 154, 93-101.
3. R. K. Jain, R. D. Locke, K. L. Matta, *Carbohydr. Res.* 1991, 212, c1-c3.
4. K. L. Matta, R. K. Jain, R. D. Locke, U.S. Pat. No. 5,438, 124A 19950801.
5. M. Izumi, O. Tsuruta, S. Harayama, H. Hashimoto, *J. Org. Chem.* 1997, 62, 992-998.
6. A. Rencurosi, L. Poletti, L. Panza, L. Lay, *J. Carbohydr. Chem.* 2001, 20, 761-765.
7. S. Komba, H. Ishada, M. Kiso, A. Hasegawa, *Bioorg. Med. Chem.* 1996, 4, 1833-1847.

ABBREVIATIONS LIST

Ac acetyl
Bn benzyl
Bz benzoyl
CAN ceric ammonium nitrate
DCM dichloromethane
DMF dimethyl formamide
DMSO dimethyl sulphoxyde
DSC differential scanning calorimetry
ESI electrospray ionization
EtOAc ethyl acetate
2'-FL 2'-O-fucosyllactose
IDCP iodinium di(sym-collidine) perchlorate
Me methyl
MeCN acetonitrile
MTBE methyl t-butyl ether
Ph phenyl
Piv pivaloyl
TBAB tetrabutyl ammonium bromide
THF tetrahydrofuran
TLC thin layer chromatography
Tr trityl
XRPD X-ray powder diffraction

| ABBREVIATIONS LIST | |
|---|---|
| Ac | acetyl |
| Bn | benzyl |
| Bz | benzoyl |
| CAN | ceric ammonium nitrate |
| DCM | dichloromethane |
| DMF | dimethyl formamide |
| DMSO | dimethyl sulphoxyde |
| DSC | differential scanning calorimetry |
| ESI | electrospray ionization |
| EtOAc | ethyl acetate |
| 2'-FL | 2'-O-fucosyllactose |
| IDCP | iodinium di(sym-collidine) perchlorate |
| Me | methyl |
| MeCN | acetonitrile |
| MTBE | methyl t-butyl ether |
| Ph | phenyl |
| Piv | pivaloyl |
| TBAB | tetrabutyl ammonium bromide |
| THF | tetrahydrofuran |
| TLC | thin layer chromatography |
| Tr | trityl |
| XRPD | X-ray powder diffraction |

The invention claimed is:

1. An O-(2,3,4-tri-O-benzyl-α-L-fucopyranosyl)-(1→2)-O-β-D-galactopyranosyl-(1→4)-D-glucose compound in crystalline form free from crystalline water

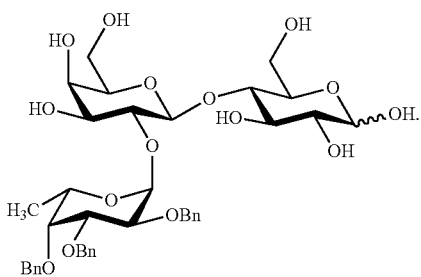

2. A method for the preparation of the compound according to claim 1, comprising the steps of:
   a) obtaining a product by mildly hydrolyzing a compound of general formula 2' by acid catalysis

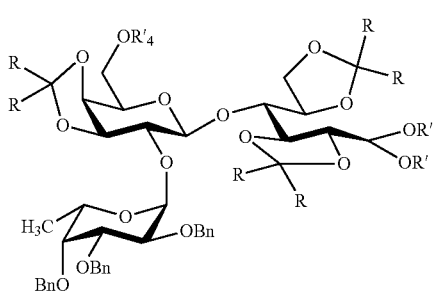

wherein $R'_4$ is acetal type group, silyl or H, R is alkyl or two geminal R-groups with the carbon atom to which they are attached form a $C_3$-$C_6$ cycloalkyl ring and R' is alkyl—or a hydrate or solvate thereof,
   b) recrystallizing the product from a $C_1$-$C_6$ alcohol or a mixture of $C_1$-$C_6$ alcohols.

3. The method according to claim 2, comprising the steps of:
   a) obtaining a product by mildly hydrolyzing a compound of general formula 2' by acid catalysis

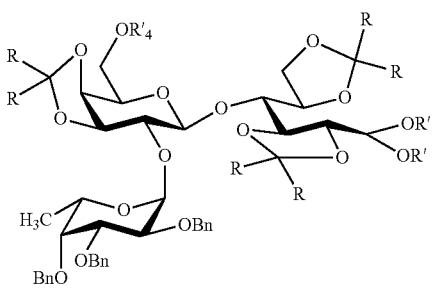

wherein $R'_4$ is acetal type group, silyl or H, R is alkyl or two geminal R-groups with the carbon atom to which they are attached form a $C_3$-$C_6$ cycloalkyl ring and R' is alkyl—or a hydrate or solvate thereof,
   b) collecting the product directly precipitated from the reaction mixture,
   c) recrystallizing the product from a $C_1$-$C_6$ alcohol or a mixture of $C_1$-$C_6$ alcohols.

4. The method according to claim 3, wherein the acid catalyzed mild hydrolysis is carried out in ethyl acetate/acetonitrile/water wherein the proportion of the ethyl acetate is more than 40 v/v %.

5. The method according to claim 3, wherein the recrystallization is conducted in methanol, ethanol or isopropanol.

6. The method according to claim 2, comprising the steps of:
   a) obtaining a product by mildly hydrolyzing a compound of general formula 2' by acid catalysis

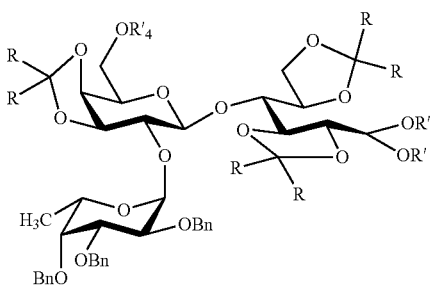

wherein $R'_4$ is acetal type group, silyl or H, R is alkyl or two geminal R-groups with the carbon atom to which they are attached form a $C_3$-$C_6$ cycloalkyl ring and R' is alkyl—or a hydrate or solvate thereof,
   b) dissolving the obtained product in a less polar aprotic solvent,
   c) extracting the product with water,
   d) isolating the product,
   e) recrystallizing the product from a $C_1$-$C_6$ alcohol or a mixture of $C_1$-$C_6$ alcohols.

7. The method according to claim 6, wherein the acid catalyzed mild hydrolysis is carried out in aqueous acetic acid.

8. The method according to claim 6, wherein the less polar aprotic solvent is an ester type solvent, and the recrystallization is conducted in methanol, ethanol or isopropanol.

9. The method according to claim 2, comprising the steps of:
   a) obtaining a crude product by mildly hydrolyzing a compound of general formula 2' by acid catalysis

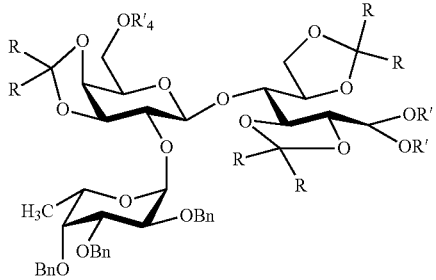

2' wherein R'$_4$ is acetal type group, silyl or H, R is alkyl or two geminal R-groups with the carbon atom to which they are attached form a C$_3$-C$_6$ cycloalkyl ring and R' is alkyl—or a hydrate or solvate thereof, and collecting the product directly precipitated from the reaction mixture, dissolving said product in a more polar aprotic solvent,
   b) diluting the dissolved product with a less polar aprotic solvent,
   c) extracting the product with water and
   d) crystallizing the product.

10. The method according to claim 2, comprising the steps of:
   a) obtaining a crude product by mildly hydrolyzing a compound of general formula 2' by acid catalysis

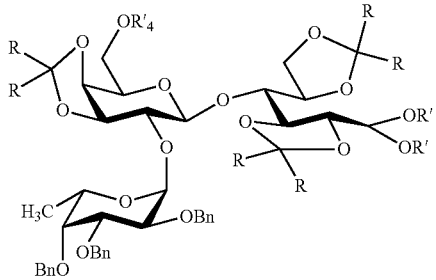

2' wherein R'$_4$ is acetal type group, silyl or H, R is alkyl or two geminal R-groups with the carbon atom to which they are attached form a C$_3$-C$_6$ cycloalkyl ring and R' is alkyl—or a hydrate or solvate thereof, dissolving the obtained material in a less polar aprotic solvent, extracting the product with water, isolating the product, and dissolving the isolated product in a more polar aprotic solvent,
   b) diluting the dissolved product with a less polar aprotic solvent,
   c) extracting the product with water and
   d) crystallizing the product.

11. The method according to claim 9 or 10, wherein the acid catalyzed mild hydrolysis is carried out in aqueous acetic acid.

12. The method according to claim 9 or 10, wherein the more polar aprotic solvent is DMSO, and the less polar aprotic solvent is an ester type solvent.

13. The method according to claim 2, characterized in that O-(2,3,4-tri-O-benzyl-α-L-fucopyranosyl)-(1→2)-O-(3,4-isopropylidene-β-D-galacto-pyranosyl)-(1→4)-2,3:5,6-di-O-isopropylidene-D-glucose dimethyl acetal is subjected to acid catalyzed mild hydrolysis.

14. A method for the preparation of 2'-O-fucosyllactose, wherein a compound of formula

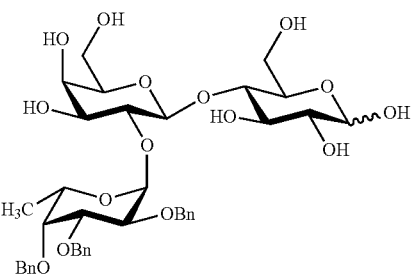

in crystalline form free from crystalline water is subjected to catalytic hydrogenolysis in a medium comprising water, or one or more C$_1$-C$_6$ alcohols, or mixtures thereof.

15. The method according to claim 14, wherein the catalytic hydrogenolysis is carried out in water, in one or more C$_1$-C$_6$ alcohols, in a mixture of water, one or more C$_1$-C$_6$ alcohols and acetic acid, in the presence of palladium on charcoal or palladium black.

16. The method according to claim 8, wherein the less polar aprotic solvent is ethyl acetate, and the recrystallization is conducted in methanol, ethanol or isopropanol.

17. The method according to claim 12, wherein the more polar aprotic solvent is DMSO, and the less polar aprotic solvent is ethyl acetate.

* * * * *